(12) United States Patent
Hull, III et al.

(10) Patent No.: US 9,388,181 B2
(45) Date of Patent: Jul. 12, 2016

(54) SUBSTITUTED 1,2,3,4-TETRAHYDROPYRIDO[3,4-E] PYRROLO[1,2-A]PYRIMIDINES AS KINASE

(71) Applicant: Allergan, Inc., Irvine, CA (US)

(72) Inventors: Clarence Eugene Hull, III, Mission Viejo, CA (US); Thomas C. Malone, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/509,002

(22) Filed: Oct. 7, 2014

(65) Prior Publication Data

US 2016/0096837 A1    Apr. 7, 2016

(51) Int. Cl.
*C07D 471/14* (2006.01)
*C07D 487/14* (2006.01)

(52) U.S. Cl.
CPC ............ *C07D 471/14* (2013.01); *C07D 487/14* (2013.01)

(58) Field of Classification Search
None
See application file for complete search history.

(56) References Cited

U.S. PATENT DOCUMENTS

| 2011/0065712 A1 | 3/2011 | Haddach et al. |
| 2013/0237538 A1* | 9/2013 | Hull, III ............... C07D 487/04 514/234.5 |

FOREIGN PATENT DOCUMENTS

| WO | 2008060488 A1 | 5/2008 |
| WO | 2009108827 A1 | 9/2009 |
| WO | 2009136813 A1 | 11/2009 |

OTHER PUBLICATIONS

J. G. Cannon Chapter Nineteen in Burger's Medicinal Chemistry and Drug Discovery, Fifth Edition, vol. I: Principles and Practice, Wiley-Interscience 1995, pp. 783-802, 784.*
CAS RN 866049-91-4 (Entered into CAS Registry Oct. 25, 2005).*
Bergers, G. et al., Benefits of targeting both pericytes and endothelial cells in the tumor vasculature with kinase inhibitors, The Journal of Clinical Investigation 2003, 111: 1287-1295 (9).
Stahl, P.H. et al., Handbook of Pharmaceutical Salts, Properties, Selection, and and Use, 2002, 330-345.
Nobuo Jo, Carolina Mailhos,et al., Inhibition of Platelet-Derived Growth Factor B Signaling Enhances the Efficacy of Anti-Vascular Endothelial Growth Factor Therapy in Multiple Models of Ocular Neovascularization, American Journal of Pathology, vol. 168, No. 6, Jun. 2006.
Justine R Smith, et al, Expression of vascular endothelial growth factor and its receptors in rosacea, Br J Ophthalmol 2007;91:226-229. doi: 10.1136/bjo.2006.101121.
S. W. Cowan-Jacob, et al., Structural biology of protein tyrosine kinases, Cell. Mol. Life Sci. 63 (2006) 2608-2625.
Regina Heidenreich, et al., Angiogenesis: The New Potential Target for the Therapy of Psoriasis?Drug News Perspect 21(2), Mar. 2008.
Aimee V. Chappelow et al., Neovascular Age-Related Macular Degeneration, Potential Therapies, Drugs 2008; 68 (8): 1029-1036.
Mark Rami Barakat, et al., VEGF inhibitors for the treatment of neovascular age-related macular degeneration, Expert Opin. Investig. Drugs (2009) 18(5).
Xinyuan Zhang, et al., Vascular endothelial growth factor—A: A multifunctional molecular player in diabetic retinopathy, The International Journal of Biochemistry & Cell Biology 41 (2009) 2368-2371.
Zhang Ni, et al., Emerging Pharmacologic Therapies for Wet Age-Related Macular Degeneration, Ophthalmologica 2009;223:401-410.
Jayne M. Stommel et al., Coactivation of Receptor Tyrosine Kinases Affects the Response of Tumor Cells to Targeted Therapies, www.sciencemag.org, Science vol. 318 Oct. 12, 2007.

* cited by examiner

*Primary Examiner* — Dennis Heyer
(74) *Attorney, Agent, or Firm* — Jonathan Bass

(57) ABSTRACT

The present invention relates to organic molecules capable of modulating tyrosine kinase signal transduction in order to regulate, modulate and/or inhibit abnormal cell proliferation.

21 Claims, No Drawings

SUBSTITUTED 1,2,3,4-TETRAHYDROPYRIDO[3,4-E] PYRROLO[1,2-A]PYRIMIDINES AS KINASE

FIELD OF THE INVENTION

The present invention relates to novel compounds capable of modulating, regulating and/or inhibiting tyrosine kinase signal transduction. The present invention is also directed to methods of regulating, modulating or inhibiting tyrosine kinases, whether of the receptor or non-receptor class, for the prevention and/or treatment of disorders related to unregulated tyrosine kinase signal transduction, including cell growth, metabolic, and blood vessel proliferative disorders.

DESCRIPTION OF THE RELATED ART

Protein tyrosine kinases (PTKs) comprise a large and diverse class of proteins having enzymatic activity. The PTKs play an important role in the control of cell growth and differentiation.

For example, receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic homeostasis, and responses to the extracellular microenvironment).

With respect to receptor tyrosine kinases, it has been shown also that tyrosine phosphorylation sites function as high-affinity binding sites for SH2 (src homology) domains of signaling molecules. Several intracellular substrate proteins that associate with receptor tyrosine kinases (RTKs) have been identified. They may be divided into two principal groups: (1) substrates which have a catalytic domain; and (2) substrates which lack such domain but serve as adapters and associate with catalytically active molecules. The specificity of the interactions between receptors or proteins and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Aberrant expression or mutations in the PTKs have been shown to lead to either uncontrolled cell proliferation (e.g. malignant tumor growth) or to defects in key developmental processes. Consequently, the biomedical community has expended significant resources to discover the specific biological role of members of the PTK family, their function in differentiation processes, their involvement in tumorigenesis and in other diseases, the biochemical mechanisms underlying their signal transduction pathways activated upon ligand stimulation and the development of novel drugs.

Tyrosine kinases can be of the receptor-type (having extracellular, transmembrane and intracellular domains) or the non-receptor type (being wholly intracellular).

The receptor-type tyrosine kinases (RTKs) comprise a large family of transmembrane receptors with diverse biological activities. The intrinsic function of RTKs is activated upon ligand binding, which results in phosphorylation of the receptor and multiple cellular substrates, and subsequently in a variety of cellular responses. The non-receptor tyrosine kinases represent a collection of cellular enzymes which lack extracellular and transmembrane sequences. A more detailed discussion of receptor and non-receptor tyrosine kinases is provided in Cowan-Jacob Cell Mol. Life Sci., 2996, 63, 2608-2625.

There are a number of examples where RTK kinases, have been found to be involved in cellular signaling pathways leading to pathological conditions, including exudative age-related macular degeneration (Ni et al. Opthalmologica 2009 223 401-410; Chappelow et al. Drugs 2008 68 1029-1036), diabetic retinopathy (Zhang et al., Int. J. Biochem. Cell Biol. 2009 41 2368-2371), cancer (Aora et al. J. Path. Exp. Ther. 2006, 315, 971), psoriasis (Heidenreich et al Drug News Perspective 2008 21 97-105), rosacea (Smith, J. R., V. B. Lanier, et al. Br J Ophthalmol 2007, 91(2): 226-229) and hyper immune response. In ophthalmic diseases such as exudative age-related macular degeneration and diabetic retinopathy aberrant activation of VEGF receptors can lead to abnormal blood vessel growth. The importance of VEGFR signaling in the exudative age-related macular degeneration disease process is evident by the clinical success of multiple anti-VEGF targeting agents including Lucentis®, Avastin®, and EYLEA™ (Barakat et al., Expert Opin. Investig. Drugs 2009, 18, 637). Recently it has been suggested that inhibition of multiple RTK signaling pathways may provide a greater therapeutic effect than targeting a single RTK signaling pathway. For example in neovascular ocular disorders such as exudative age-related macular degeneration and diabetic retinopathy the inhibition of both VEGFR and PDGFRβ may provide a greater therapeutic effect by causing regression of existing neovascular blood vessels present in the disease (Adamis et al., Am. J. Pathol. 2006 168 2036-2053). In cancer inhibition of multiple RTK signaling pathways has been suggested to have a greater effect than inhibiting a single RTK pathway (DePinho et al., Science 2007 318 287-290; Bergers et al. J. Clin Invest. 2003 111 1287-1295).

The identification of effective small compounds which specifically inhibit signal transduction by modulating the activity of receptor and non-receptor tyrosine kinases to regulate and modulate abnormal or inappropriate cell proliferation is therefore desirable and one object of this invention.

SUMMARY OF THE INVENTION

The present invention relates to organic molecules capable of modulating, regulating and/or inhibiting tyrosine kinase signal transduction by blocking the VEGF and/or PDGF receptors. Such compounds are useful for the treatment of diseases related to unregulated PTKs transduction, including cell proliferative diseases such as cancer; vascular (blood vessel) proliferative disorders such as mesangial cell proliferative disorders and metabolic diseases, lung carcinomas, breast carcinomas, Non Hodgkin's lymphomas, ovarian carcinoma, pancreatic cancer, malignant pleural mesothelioma, melanoma, arthritis, restenosis, hepatic cirrhosis, atherosclerosis, psoriasis, rosacea, diabetic mellitus, wound healing and inflammation and preferably ophthalmic diseases, i.e. diabetic retinopathy, retinopathy of prematurity, macular edema, retinal vein occlusion, exudative or neovascular age-related macular degeneration, high-risk eyes (i.e. fellow eyes have neovascular age-related macular degeneration) with dry age-related macular degeneration, neovascular disease associated with retinal vein occlusion, neovascular disease (including choroidal neovascularization) associated with the following: pathologic myopia, pseudoxanthoma elasticum, optic nerve drusen, traumatic choroidal rupture, central serous retinopathy, cystoid macular edema, diabetic retinopathy, proliferative diabetic retinopathy, diabetic macular edema, rubeosis iridis, retinopathy of prematurity, Central and branch retinal vein occlusions, inflammatory/infectious retinal, neovascularization/edema, corneal neovascularization, hyperemia related to an actively inflamed pterygia, recurrent pterygia following excisional surgery, post-excision, progressive pterygia approaching the visual axis, prophylactic therapy to prevent recurrent pterygia, of post-excision, progressive pterygia approaching the visual axis, chronic low grade hyperemia associated with pterygia, neovascular glaucoma, iris neovascularization, idiopathic etiologies, presumed ocular histoplasmosis syndrome, retinopathy of prematurity, chronic allergic conjunctivitis, ocular rosacea, blepharoconjunctivitis, recurrent episcleritis, keratoconjunctivitis sicca, ocular graft vs host disease, etc.

In one aspect, the invention provides a compound represented by Formula I or a pharmaceutically acceptable salt thereof or stereoisomeric forms thereof, or the enantiomers, diastereoisomers, tautomers, zwitterions and pharmaceutically acceptable salts thereof:

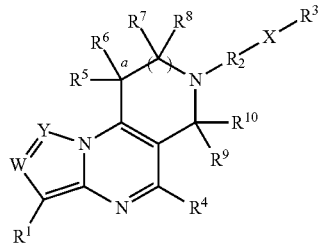

I wherein:
$R^1$ is H or $NR^{13a}R^{14a}$;
$R^2$ is substituted or unsubstituted heterocyle or is substituted or unsubstituted aryl;
$R^3$ is substituted or unsubstituted heterocyle or is substituted or unsubstituted aryl;
$R^4$ is H or $NR^{13a}R^{14a}$;
$R^5$ is H or substituted or unsubstituted $C_{1-8}$ alkyl;
$R^6$ is H or substituted or unsubstituted $C_{1-8}$ alkyl;
$R^7$ is H or substituted or unsubstituted $C_{1-8}$ alkyl;
$R^8$ is H or substituted or unsubstituted $C_{1-8}$ alkyl;
$R^9$ is H or substituted or unsubstituted $C_{1-8}$ alkyl;
$R^{10}$ is H or substituted or unsubstituted $C_{1-8}$ alkyl;
X is

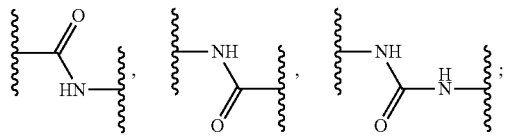 [SMILES: *NC(*)=O ; *NC(*)=O ; *NC(=O)N*]

Y is $CR^{11}$ or N;
W is $CR^{12}$ or N;

$R^{11}$ is hydrogen, halogen, $C(O)OR^{17}$, $CF_3$, $C_1$ to $C_8$ alkyl, $NR^{13a}R^{14a}$, $C(O)NR^{13a}R^{14a}$, $(CR^{15}R^{16})_pNR^{13a}R^{14a}$, $(CR^{15}R^{16})_pC(O)OR^{17}$, $(CR^{15}R^{16})_pOR^{17}$, $NR^{13}C(O)(CR^{15}R^{16})_pNR^{13a}R^{14a}$, $NR^{13}C(O)(CR^{15}R^{16})_pC(O)OR^{17}$, $NR^{13}C(O)(CR^{15}R^{16})_pOR^{17}$, $C(O)(CR^{15}R^{16})_pNR^{13a}R^{14a}$, $C(O)(CR^{15}R^{16})_pC(O)OR^{17}$, $C(O)(CR^{15}R^{16})_pCOR^{17}$, $C(O)NR^{13}(CR^{15}R^{16})_pNR^{13}R^{14}$, $C(O)NR^{13}(CR^{15}R^{16})_pC(O)OR^{17}$, $C(O)NR^{13}(CR^{15}R^{16})_pCOR^{17}$, $NR^{13}C(O)NR^{14}(CR^{15}R^{16})_pNR^{13}R^{14}$, $NR^{13}C(O)NR^{14}(CR^{15}R^{16})_pC(O)OR^{17}$, or $NR^{13}C(O)NR^{14}(CR^{15}R^{18})_pOR^{17}$;

$R^{12}$ is hydrogen, halogen, $C(O)OR^{17}$, $CF_3$, $C_1$ to $C_8$ alkyl, $NR^{13a}R^{14a}$, $C(O)NR^{13a}R^{14a}$, $(CR^{15}R^{16})_pNR^{13a}R^{14a}$, $(CR^{15}R^{16})_pC(O)OR^{17}$, $(CR^{15}R^{16})_pOR^{17}$, $NR^{13}C(O)(CR^{15}R^{16})_pNR^{13}R^{14}$, $NR^{13}C(O)(CR^{15}R^{16})_pC(O)OR^{17}$, $NR^{13}C(O)(CR^{15}R^{16})_pOR^{17}$, $C(O)(CR^{15}R^{16})_pNR^{1a3}R^{14a}$, $C(O)(CR^{15}R^{16})_pC(O)OR^{17}$, $C(O)(CR^{15}R^{16})_pCOR^{17}$, $C(O)NR^{13}(CR^{15}R^{16})_pNR^{13}R^{14}$, $C(O)NR^{13}(CR^{15}R^{16})_pC(O)OR^{17}$, $C(O)NR^{13}(CR^{15}R^{16})_pCOR^{17}$, $NR^{13}C(O)NR^{14}(CR^{15}R^{16})_pNR^{13a}R^{14a}$, $NR^{13}C(O)NR^{14}(CR^{15}R^{16})_pC(O)OR^{17}$, or $NR^{13}C(O)NR^{14}(CR^{15}R^{16})_pOR^{17}$;

$R^{13}$ is H or substituted or unsubstituted $C_{1-8}$ alkyl;
$R^{14}$ is H or substituted or unsubstituted $C_{1-8}$ alkyl;
$R^{13a}$ is H, substituted or unsubstituted $C_{1-8}$ alkyl or together with $R^{14a}$ and the N can form a substituted or unsubstituted heterocycle;
$R^{14a}$ is H, substituted or unsubstituted $C_{1-8}$ alkyl or together with $R^{13a}$ and the N can form a substituted or unsubstituted heterocycle;
$R^{15}$ is H, halogen, hydroxyl, $CF_3$, or substituted or unsubstituted $C_{1-8}$ alkyl;
$R^{16}$ is H halogen, hydroxyl, $CF_3$, or substituted or unsubstituted $C_{1-8}$ alkyl;
$R^{17}$ is H or substituted or unsubstituted $C_{1-8}$ alkyl;
a is 0 or 1; and
p is 1, 2, 3 or 4.

In another aspect, the invention provides a compound represented by Formula I wherein:
$R^1$ is H or $NR^{13a}R^{14a}$;
$R^2$ is substituted or unsubstituted heterocycle or substituted or unsubstituted aryl;
$R^3$ is substituted or unsubstituted heterocycle or substituted or unsubstituted aryl;
$R^4$ is H or $NR^{13a}R^{14a}$;
$R^5$ is H or substituted or unsubstituted $C_{1-8}$ alkyl;
$R^6$ is H or substituted or unsubstituted $C_{1-8}$ alkyl;
$R^9$ is H or substituted or unsubstituted $C_{1-8}$ alkyl;
$R^{10}$ is H or substituted or unsubstituted $C_{1-8}$ alkyl;
X is

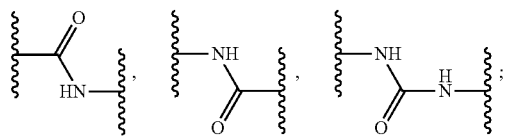 [SMILES: *NC(*)=O ; *NC(*)=O ; *NC(=O)N*]

Y is $CR^{11}$ or N;
W is $CR^{12}$ or N;
$R^{11}$ is hydrogen, halogen, $C(O)OR^{17}$, $CF_3$, $C_1$ to $C_8$ alkyl, $NR^{13a}R^{14a}$, $C(O)NR^{13a}R^{14a}$, $(CR^{15}R^{16})_pNR^{13a}R^{14a}$, $(CR^{15}R^{16})_pC(O)OR^{17}$, $(CR^{15}R^{16})_pOR^{17}$, $NR^{13}C(O)(CR^{15}R^{16})_pNR^{13a}R^{14a}$, $NR^{13}C(O)(CR^{15}R^{16})_pC(O)OR^{17}$, $NR^{13}C(O)(CR^{15}R^{16})_pOR^{17}$, $C(O)(CR^{15}R^{16})_pNR^{13a}R^{14a}$, $C(O)(CR^{15}R^{16})_pC(O)OR^{17}$, $C(O)(CR^{15}R^{16})_pCOR^{17}$, $C(O)NR^{13}(CR^{15}R^{16})_pNR^{13}R^{14}$, $C(O)NR^{13}(CR^{15}R^{16})_pC(O)OR^{17}$, $C(O)NR^{13}(CR^{15}R^{16})_pCOR^{17}$, $NR^{13}C(O)NR^{14}$ $(CR^{15}R^{16})_pNR^{13}R^{14}$, $NR^{13}C(O)NR^{14}(CR^{15}R^{16})_pC(O)OR^{17}$, $NR^{13}C(O)NR^{14}(CR^{15}R^{16})_pOR^{17}$;

$R^{12}$ is hydrogen, halogen, $C(O)OR^{17}$, $CF_3$, $C_1$ to $C_8$ alkyl, $NR^{13a}R^{14a}$, $C(O)NR^{13a}R^{14a}$, $(CR^{15}R^{16})_pNR_{13a}R^{14a}$, $(CR^{15}R^{16})_pC(O)OR^{17}$, $(CR^{15}R^{16})_pOR^{17}$, $NR^{13}C(O)(CR^{15}R^{16})_pNR^{13}R^{14}$, $NR^{13}C(O)(CR^{15}R^{16})_pC(O)OR^{17}$, $NR^{13}C(O)(CR^{15}R^{16})_pOR^{17}$, $C(O)(CR^{15}R^{16})_pNR^{1a3}R^{14a}$, $C(O)(CR^{15}R^{16})_pC(O)OR^{17}$, $C(O)(CR^{15}R^{16})_pCOR^{17}$, $C(O)NR^{13}(CR^{15}R^{16})_pNR^{13}R^{14}$, $C(O)NR^{13}(CR^{15}R^{16})_pC(O)OR^{17}$, $C(O)NR^{13}(CR^{15}R^{16})_pCOR^{17}$, $NR^{13}C(O)NR^{14}(CR^{15}R^{16})_pNR^{13a}R^{14a}$, $NR^{13}C(O)NR^{14}(CR^{15}R^{16})_pC(O)OR^{17}$, $NR^{13}C(O)NR^{14}(CR^{15}R^{16})_pOR^{17}$;

$R^{13}$ is H or substituted or unsubstituted $C_{1-8}$ alkyl;
$R^{14}$ is H or substituted or unsubstituted $C_{1-8}$ alkyl;
$R^{13a}$ is H, substituted or unsubstituted $C_{1-8}$ alkyl or together with $R^{14a}$ and the N can form a substituted or unsubstituted heterocycle;
$R^{14a}$ is H, substituted or unsubstituted $C_{1-8}$ alkyl or together with $R^{13a}$ and the N can form a substituted or unsubstituted heterocycle;
$R^{15}$ is H, halogen, hydroxyl, $CF_3$ or substituted or unsubstituted $C_{1-8}$ alkyl;
$R^{16}$ is H halogen, hydroxyl, $CF_3$ or substituted or unsubstituted $C_{1-8}$ alkyl;
$R^{17}$ is H or substituted or unsubstituted $C_{1-8}$ alkyl;
a is 0; and
p is 1, 2, 3 or 4.

In another aspect, the invention provides a compound represented by Formula I wherein:
$R^1$ is H or $NR^{13a}R^{14a}$;
$R^2$ is substituted or unsubstituted heterocyle or substituted or unsubstituted aryl;
$R^3$ is substituted or unsubstituted heterocyle or substituted or unsubstituted aryl;
$R^4$ is H or $NR^{13a}R^{14a}$;
$R^5$ is H or substituted or unsubstituted $C_{1-8}$ alkyl;
$R^6$ is H or substituted or unsubstituted $C_{1-8}$ alkyl;
$R^7$ is H or substituted or unsubstituted $C_{1-8}$ alkyl;
$R^8$ is H or substituted or unsubstituted $C_{1-8}$ alkyl;
$R^9$ is H or substituted or unsubstituted $C_{1-8}$ alkyl;
$R^{10}$ is H or substituted or unsubstituted $C_{1-8}$ alkyl;
X is

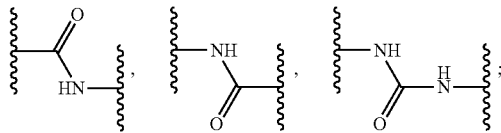 [SMILES: *NC(*)=O ; *NC(*)=O ; *NC(=O)N*]

Y is $CR^{11}$ or N;
W is $CR^{12}$ or N;
$R^{11}$ is hydrogen, halogen, $C(O)OR^{17}$, $CF_3$, $C_1$ to $C_8$ alkyl, $NR^{13a}R^{14a}$, $C(O)NR^{13a}R^{14a}$, $(CR^{15}R^{16})_pNR^{13a}R^{14a}$, $(CR^{15}R^{16})_pC(O)OR^{17}$, $(CR^{15}R^{16})_pOR^{17}$, $NR^{13}C(O)(CR^{15}R^{16})_pNR^{13a}R^{14a}$, $NR^{13}C(O)(CR^{15}R^{16})_pC(O)OR^{17}$, $NR^{13}C(O)(CR^{15}R^{16})_pOR^{17}$, $C(O)(CR^{15}R^{16})_pNR^{13a}R^{14a}$, $C(O)(CR^{15}R^{16})_pC(O)OR^{17}$, $C(O)(CR^{15}R^{16})_pCOR^{17}$, $C(O)NR^{13}(CR^{15}R^{16})_pNR^{13}R^{14}$, $C(O)NR^{13}(CR^{15}R^{16})_pC(O)OR^{17}$, $C(O)NR^{13}(CR^{15}R^{16})_pCOR^{17}$, $NR^{13}C(O)NR^{14}(CR^{15}R^{16})_pNR^{13}R^{14}$, $NR^{13}C(O)NR^{14}(CR^{15}R^{16})_pC(O)OR^{17}$, $NR^{13}C(O)NR^{14}(CR^{15}R^{16})_pOR^{17}$;

$R^{12}$ is hydrogen, halogen, $C(O)OR^{17}$, $CF_3$, $C_1$ to $C_8$ alkyl, $NR^{13a}R^{14a}$, $C(O)NR^{13a}R^{14a}$, $(CR^{15}R^{16})_pNR^{13a}R^{14a}$, $(CR^{15}R^{16})_pC(O)OR^{17}$, $(CR^{15}R^{16})_pOR^{17}$, $NR^{13}C(O)(CR^{15}R^{16})_pNR^{13}R^{14}$, $NR^{13}C(O)(CR^{15}R^{16})_pC(O)OR^{17}$, $NR^{13}C(O)(CR^{15}R^{16})_pOR^{17}$, $C(O)(CR^{15}R^{16})_pNR^{1a3}R^{14a}$, $C(O)(CR^{15}R^{16})_pC(O)OR^{17}$, $C(O)(CR^{15}R^{16})_pCOR^{17}$, $C(O)NR^{13}(CR^{15}R^{16})_pNR^{13}R^{14}$, $C(O)NR^{13}(CR^{15}R^{16})_pC(O)OR^{17}$, $C(O)NR^{13}(CR^{15}R^{16})_pCOR^{17}$, $NR^{13}C(O)NR^{14}(CR^{15}R^{16})_pNR^{13a}R^{14a}$, $NR^{13}C(O)NR^{14}(CR^{15}R^{16})_pC(O)OR^{17}$, $NR^{13}C(O)NR^{14}(CR^{15}R^{16})_pOR^{17}$;

$R^{13}$ is H or substituted or unsubstituted $C_{1-8}$ alkyl;
$R^{14}$ is H or substituted or unsubstituted $C_{1-8}$ alkyl;
$R^{13a}$ is H, substituted or unsubstituted $C_{1-8}$ alkyl or together with $R^{14a}$ and the N can form a substituted or unsubstituted heterocycle;
$R^{14a}$ is H, substituted or unsubstituted $C_{1-8}$ alkyl or together with $R^{13a}$ and the N can form a substituted or unsubstituted heterocycle;
$R^{15}$ is H, halogen, hydroxyl, $CF_3$ or substituted or unsubstituted $C_{1-8}$ alkyl;
$R^{16}$ is H halogen, hydroxyl, $CF_3$ or substituted or unsubstituted $C_{1-8}$ alkyl;
$R^{17}$ is H or substituted or unsubstituted $C_{1-8}$ alkyl;
a is 1; and
p is 1, 2, 3 or 4.

In another aspect, the invention provides a compound represented by Formula I wherein:
$R^1$ is H or $NR^{13a}R^{14a}$;
$R^2$ is substituted or unsubstituted heterocyle or substituted or unsubstituted aryl;
$R^3$ is substituted or unsubstituted heterocyle or substituted or unsubstituted aryl;
$R^4$ is H or $NR^{13a}R^{14a}$;
$R^5$ is H or substituted or unsubstituted $C_{1-8}$ alkyl;
$R^6$ is H or substituted or unsubstituted $C_{1-8}$ alkyl;
$R^7$ is H or substituted or unsubstituted $C_{1-8}$ alkyl;
$R^8$ is H or substituted or unsubstituted $C_{1-8}$ alkyl;
$R^9$ is H or substituted or unsubstituted $C_{1-8}$ alkyl;
$R^{10}$ is H or substituted or unsubstituted $C_{1-8}$ alkyl;
X is

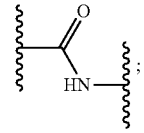

Y is $CR^{11}$ or N;
W is $CR^{12}$ or N;
$R^{11}$ is hydrogen, halogen, $C(O)OR^{17}$, $CF_3$, $C_1$ to $C_8$ alkyl, $NR^{13a}R^{14a}$, $C(O)NR^{13a}R^{14a}$, $(CR^{15}R^{16})_pNR^{13a}R^{14a}$, $(CR^{15}R^{16})_pC(O)OR^{17}$, $(CR^{15}R^{16})_pOR^{17}$, $NR^{13}C(O)(CR^{15}R^{16})_pNR^{13a}R^{14a}$, $NR^{13}C(O)(CR^{15}R^{16})_pC(O)OR^{17}$, $NR^{13}C(O)(CR^{15}R^{16})_pOR^{17}$, $C(O)(CR^{15}R^{16})_pNR^{13a}R^{14a}$, $C(O)(CR^{15}R^{16})_pC(O)OR^{17}$, $C(O)(CR^{15}R^{16})_pCOR^{17}$, $C(O)NR^{13}(CR^{15}R^{16})_pNR^{13}R^{14}$, $C(O)NR^{13}(CR^{15}R^{16})_pC(O)OR^{17}$, $C(O)NR^{13}(CR^{15}R^{16})_pCOR^{17}$, $NR^{13}C(O)NR^{14}(CR^{15}R^{16})_pNR^{13}R^{14}$, $NR^{13}C(O)NR^{14}(CR^{15}R^{16})_pC(O)OR^{17}$, $NR^{13}C(O)NR^{14}(CR^{15}R^{16})_pOR^{17}$;

$R^{13}$ is H or substituted or unsubstituted $C_{1-8}$ alkyl;
$R^{14}$ is H or substituted or unsubstituted $C_{1-8}$ alkyl;
$R^{13a}$ is H, substituted or unsubstituted $C_{1-8}$ alkyl or together with $R^{14a}$ and the N can form a substituted or unsubstituted heterocycle;
$R^{14a}$ is H, substituted or unsubstituted $C_{1-8}$ alkyl or together with $R^{13a}$ and the N can form a substituted or unsubstituted heterocycle;
$R^{15}$ is H, halogen, hydroxyl, $CF_3$ or substituted or unsubstituted $C_{1-8}$ alkyl;
$R^{16}$ is H halogen, hydroxyl, $CF_3$ or substituted or unsubstituted $C_{1-8}$ alkyl;
$R^{17}$ is H or substituted or unsubstituted $C_{1-8}$ alkyl;
a is 1; and
p is 1, 2, 3 or 4.

In another aspect, the invention provides a compound represented by Formula I wherein:
$R^1$ is H or $NR^{13a}R^{14a}$;
$R^2$ is substituted or unsubstituted heterocycle or substituted or unsubstituted aryl;
$R^3$ is substituted or unsubstituted heterocycle or substituted or unsubstituted aryl;
$R^4$ is H or $NR^{13a}R^{14a}$;
$R^5$ is H or substituted or unsubstituted $C_{1-8}$ alkyl;
$R^6$ is H or substituted or unsubstituted $C_{1-8}$ alkyl;
$R^7$ is H or substituted or unsubstituted $C_{1-8}$ alkyl;
$R^8$ is H or substituted or unsubstituted $C_{1-8}$ alkyl;
$R^9$ is H or substituted or unsubstituted $C_{1-8}$ alkyl;
$R^{10}$ is H or substituted or unsubstituted $C_{1-8}$ alkyl;
X is Y is $CR^{11}$ or N;
W is $CR^{12}$ or N;
$R^{11}$ is hydrogen, halogen, $C(O)OR^{17}$, $CF_3$, $C_1$ to $C_8$ alkyl, $NR^{13a}R^{14a}$, $C(O)NR^{13a}R^{14a}$, $(CR^{15}R^{16})_pNR^{13a}R^{14a}$, $(CR^{15}R^{16})_pC(O)OR^{17}$, $(CR^{15}R^{16})_pOR^{17}$, $NR^{13}C(O)(CR^{15}R^{16})_pNR^{13a}R^{14a}$, $NR^{13}C(O)(CR^{15}R^{16})_pC(O)OR^{17}$, $NR^{13}C(O)(CR^{15}R^{16})_pOR^{17}$, $C(O)(CR^{15}R^{16})_pNR^{13a}R^{14a}$, $C(O)(CR^{15}R^{16})_pC(O)OR^{17}$, $C(O)(CR^{15}R^{16})_pCOR^{17}$, $C(O)NR^{13}(CR^{15}R^{16})_pNR^{13}R^{14}$, $C(O)NR^{13}(CR^{15}R^{16})_pC(O)OR^{17}$, $C(O)NR^{13}(CR^{15}R^{16})_pCOR^{17}$, $NR^{13}C(O)NR^{14}(CR^{15}R^{16})_pNR^{13}R^{14}$, $NR^{13}C(O)NR^{14}(CR^{15}R^{16})_pC(O)OR^{17}$, $NR^{13}C(O)NR^{14}(CR^{15}R^{16})_pOR^{17}$;
$R^{12}$ is hydrogen, halogen, $C(O)OR^{17}$, $CF_3$, $C_1$ to $C_8$ alkyl, $NR^{13a}R^{14a}$, $C(O)NR^{13a}R^{14a}$, $(CR^{15}R^{16})_pNR^{13a}R^{14a}$, $(CR^{15}R^{16})_pC(O)OR^{17}$, $(CR^{15}R^{16})_pOR^{17}$, $NR^{13}C(O)(CR^{15}R^{16})_pNR^{13}R^{14}$, $NR^{13}C(O)(CR^{15}R^{16})_pC(O)OR^{17}$, $NR^{13}C(O)(CR^{15}R^{16})_pOR^{17}$, $C(O)(CR^{15}R^{16})_pNR^{1a3}R^{14a}$, $C(O)(CR^{15}R^{16})_pC(O)OR^{17}$, $C(O)(CR^{15}R^{16})_pCOR^{17}$, $C(O)NR^{13}(CR^{15}R^{16})_pNR^{13}R^{14}$, $C(O)NR^{13}(CR^{15}R^{16})_pC(O)OR^{17}$, $C(O)NR^{13}(CR^{15}R^{16})_pCOR^{17}$, $NR^{13}C(O)NR^{14}(CR^{15}R^{16})_pNR^{13a}R^{14a}$, $NR^{13}C(O)NR^{14}(CR^{15}R^{16})_pC(O)OR^{17}$, $NR^{13}C(O)NR^{14}(CR^{15}R^{16})_pOR^{17}$;
$R^{13}$ is H or substituted or unsubstituted $C_{1-8}$ alkyl;
$R^{14}$ is H or substituted or unsubstituted $C_{1-8}$ alkyl;
$R^{13a}$ is H, substituted or unsubstituted $C_{1-8}$ alkyl or together with $R^{14a}$ and the N can form a substituted or unsubstituted heterocycle;
$R^{14a}$ is H, substituted or unsubstituted $C_{1-8}$ alkyl or together with $R^{13a}$ and the N can form a substituted or unsubstituted heterocycle;
$R^{15}$ is H, halogen, hydroxyl, $CF_3$ or substituted or unsubstituted $C_{1-8}$ alkyl;
$R^{16}$ is H halogen, hydroxyl, $CF_3$ or substituted or unsubstituted $C_{1-8}$ alkyl;
$R^{17}$ is H or substituted or unsubstituted $C_{1-8}$ alkyl;
a is 1; and
p is 1, 2, 3 or 4.

In another aspect, the invention provides a compound represented by Formula I wherein:
$R^1$ is H or $NR^{13a}R^{14a}$;
$R^2$ is substituted or unsubstituted heterocycle or substituted or unsubstituted aryl;
$R^3$ is substituted or unsubstituted heterocycle or substituted or unsubstituted aryl;
$R^4$ is H or $NR^{13a}R^{14a}$;
$R^5$ is H or substituted or unsubstituted $C_{1-8}$ alkyl;
$R^6$ is H or substituted or unsubstituted $C_{1-8}$ alkyl;
$R^7$ is H or substituted or unsubstituted $C_{1-8}$ alkyl;
$R^8$ is H or substituted or unsubstituted $C_{1-8}$ alkyl;
$R^9$ is H or substituted or unsubstituted $C_{1-8}$ alkyl;
$R^{10}$ is H or substituted or unsubstituted $C_{1-8}$ alkyl;
X is Y is $CR^{11}$ or N;
W is $CR^{12}$ or N;
$R^{11}$ is hydrogen, halogen, $C(O)OR^{17}$, $CF_3$, $C_1$ to $C_8$ alkyl, $NR^{13a}R^{14a}$, $C(O)NR^{13a}R^{14a}$, $(CR^{15}R^{16})_pNR^{13a}R^{14a}$, $(CR^{15}R^{16})_pC(O)OR^{17}$, $(CR^{15}R^{16})_pOR^{17}$, $NR^{13}C(O)(CR^{15}R^{16})_pNR^{13}R^{14}$, $NR^{13}C(O)(CR^{15}R^{16})_pC(O)OR^{17}$, $NR^{13}C(O)(CR^{15}R^{16})_pOR^{17}$, $C(O)(CR^{15}R^{16})_pNR^{13a}R^{14a}$, $C(O)(CR^{15}R^{16})_pC(O)OR^{17}$, $C(O)(CR^{15}R^{16})_pCOR^{17}$, $C(O)NR^{13}(CR^{15}R^{16})_pNR^{13}R^{14}$, $C(O)NR^{13}(CR^{15}R^{16})_pC(O)OR^{17}$, $C(O)NR^{13}(CR^{15}R^{16})_pCOR^{17}$, $NR^{13}C(O)NR^{14}(CR^{15}R^{16})_pNR^{13}R^{14}$, $NR^{13}C(O)NR^{14}(CR^{15}R^{16})_pC(O)OR^{17}$, $NR^{13}C(O)NR^{14}(CR^{15}R^{16})_pOR^{17}$;
$R^{12}$ is hydrogen, halogen, $C(O)OR^{17}$, $CF_3$, $C_1$ to $C_8$ alkyl, $NR^{13a}R^{14a}$, $C(O)NR^{13a}R^{14a}$, $(CR^{15}R^{16})_pNR^{13a}R^{14a}$, $(CR^{15}R^{16})_pC(O)OR^{17}$, $(CR^{15}R^{16})_pOR^{17}$, $NR^{13}C(O)(CR^{15}R^{16})_pNR^{13}R^{14}$, $NR^{13}C(O)(CR^{15}R^{16})_pC(O)OR^{17}$, $NR^{13}C(O)(CR^{15}R^{16})_pOR^{17}$, $C(O)(CR^{15}R^{16})_pNR^{1a3}R^{14a}$, $C(O)(CR^{15}R^{16})_pC(O)OR^{17}$, $C(O)(CR^{15}R^{16})_pCOR^{17}$, $C(O)NR^{13}(CR^{15}R^{16})_pNR^{13}R^{14}$, $C(O)NR^{13}(CR^{15}R^{16})_pC(O)OR^{17}$, $C(O)NR^{13}(CR^{15}R^{16})_pCOR^{17}$, $NR^{13}C(O)NR^{14}(CR^{15}R^{16})_pNR^{13a}R^{14a}$, $NR^{13}C(O)NR^{14}(CR^{15}R^{16})_pC(O)OR^{17}$, $NR^{13}C(O)NR^{14}(CR^{15}R^{16})_pOR^{17}$;
$R^{13}$ is H or substituted or unsubstituted $C_{1-8}$ alkyl;
$R^{14}$ is H or substituted or unsubstituted $C_{1-8}$ alkyl;
$R^{13a}$ is H, substituted or unsubstituted $C_{1-8}$ alkyl or together with $R^{14a}$ and the N can form a substituted or unsubstituted heterocycle;
$R^{14a}$ is H, substituted or unsubstituted $C_{1-8}$ alkyl or together with $R^{13a}$ and the N can form a substituted or unsubstituted heterocycle;
$R^{15}$ is H, halogen, hydroxyl, $CF_3$ or substituted or unsubstituted $C_{1-8}$ alkyl;

$R^{16}$ is H halogen, hydroxyl, $CF_3$ or substituted or unsubstituted $C_{1-8}$ alkyl;
$R^{17}$ is H or substituted or unsubstituted $C_{1-8}$ alkyl;
a is 1; and
p is 1, 2, 3 or 4.

In another aspect, the invention provides a compound represented by Formula I wherein:
$R^1$ is H or $NR^{13a}R^{14a}$;
$R^2$ is substituted or unsubstituted heterocyle or substituted or unsubstituted aryl;
$R^3$ is substituted or unsubstituted heterocyle or substituted or unsubstituted aryl;
$R^4$ is H or $NR^{13a}R^{14a}$;
$R^5$ is H or substituted or unsubstituted $C_{1-8}$ alkyl;
$R^6$ is H or substituted or unsubstituted $C_{1-8}$ alkyl;
$R^7$ is H or substituted or unsubstituted $C_{1-8}$ alkyl;
$R^8$ is H or substituted or unsubstituted $C_{1-8}$ alkyl;
$R^9$ is H or substituted or unsubstituted $C_{1-8}$ alkyl;
$R^{10}$ is H or substituted or unsubstituted $C_{1-8}$ alkyl;
X is

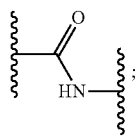 [SMILES: *NC(*)=O]

Y is $CR^{11}$ or N;
W is $CR^{12}$ or N;
$R^{11}$ is hydrogen, halogen, $C(O)OR^{17}$, $CF_3$, $C_1$ to $C_8$ alkyl, $NR^{13a}R^{14a}$, $C(O)NR^{13a}R^{14a}$, $(CR^{15}R^{16})_pNR^{13a}R^{14a}$, $(CR^{15}R^{16})_pC(O)OR^{17}$, $(CR^{15}R^{16})_pOR^{17}$, $NR^{13}C(O)(CR^{15}R^{16})_pNR^{13a}R^{14a}$, $NR^{13}C(O)(CR^{15}R^{16})_pC(O)OR^{17}$, $NR^{13}C(O)(CR^{15}R^{16})_pOR^{17}$, $C(O)(CR^{15}R^{16})_pNR^{13a}R^{14a}$, $C(O)(CR^{15}R^{16})_pC(O)OR^{17}$, $C(O)(CR^{15}R^{16})_pCOR^{17}$, $C(O)NR^{13}(CR^{15}R^{16})_pNR^{13}R^{14}$, $C(O)NR^{13}(CR^{15}R^{16})_pC(O)OR^{17}$, $C(O)NR^{13}(CR^{15}R^{16})_pCOR^{17}$, $NR^{13}C(O)NR^{14}(CR^{15}R^{16})_pNR^{13}R^{14}$, $NR^{13}C(O)NR^{14}(CR^{15}R^{16})_pC(O)OR^{17}$, $NR^{13}C(O)NR^{14}(CR^{15}R^{16})_pOR^{17}$;
$R^{12}$ is hydrogen, halogen, $C(O)OR^{17}$, $CF_3$, $C_1$ to $C_8$ alkyl, $NR^{13a}R^{14a}$, $C(O)NR^{13a}R^{14a}$, $(CR^{15}R^{16})_pNR^{13a}R^{14a}$, $(CR^{15}R^{16})_pC(O)OR^{17}$, $(CR^{15}R^{16})_pOR^{17}$, $NR^{13}C(O)(CR^{15}R^{16})_pNR^{13}R^{14}$, $NR^{13}C(O)(CR^{15}R^{16})_pC(O)OR^{17}$, $NR^{13}C(O)(CR^{15}R^{16})_pOR^{17}$, $C(O)(CR^{15}R^{16})_pNR^{1a3}R^{14a}$, $C(O)(CR^{15}R^{16})_pC(O)OR^{17}$, $C(O)(CR^{15}R^{16})_pCOR^{17}$, $C(O)NR^{13}(CR^{15}R^{16})_pNR^{13}R^{14}$, $C(O)NR^{13}(CR^{15}R^{16})_pC(O)OR^{17}$, $C(O)NR^{13}(CR^{15}R^{16})_pCOR^{17}$, $NR^{13}C(O)NR^{14}(CR^{15}R^{16})_pNR^{13a}R^{14a}$, $NR^{13}C(O)NR^{14}(CR^{15}R^{16})_pC(O)OR^{17}$, $NR^{13}C(O)NR^{14}(CR^{15}R^{16})_pOR^{17}$;
$R^{13}$ is H or substituted or unsubstituted $C_{1-8}$ alkyl;
$R^{14}$ is H or substituted or unsubstituted $C_{1-8}$ alkyl;
$R^{13a}$ is H, substituted or unsubstituted $C_{1-8}$ alkyl or together with $R^{14a}$ and the N can form a substituted or unsubstituted heterocycle;
$R^{14a}$ is H, substituted or unsubstituted $C_{1-8}$ alkyl or together with $R^{13a}$ and the N can form a substituted or unsubstituted heterocycle;
$R^{15}$ is H, halogen, hydroxyl, $CF_3$ or substituted or unsubstituted $C_{1-8}$ alkyl;
$R^{16}$ is H halogen, hydroxyl, $CF_3$ or substituted or unsubstituted $C_{1-8}$ alkyl;
$R^{17}$ is H or substituted or unsubstituted $C_{1-8}$ alkyl;
a is 0; and
p is 1, 2, 3 or 4.

In another aspect, the invention provides a compound represented by Formula I wherein:
$R^1$ is H;
$R^2$ is substituted or unsubstituted heterocyle or substituted or unsubstituted aryl;
$R^3$ is substituted or unsubstituted heterocyle or substituted or unsubstituted aryl;
$R^4$ is H;
$R^5$ is H;
$R^6$ is H;
$R^7$ is H;
$R^8$ is H;
$R^9$ is H;
$R^{10}$ is H;
X is

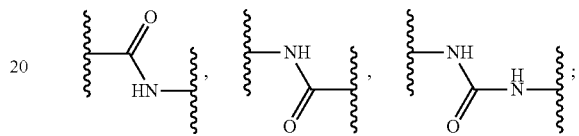

Y is N;
W is $CR^{12}$;
$R^{12}$ is hydrogen, $C(O)OR^{17}$;
$R^{17}$ is H or substituted or unsubstituted $C_{1-8}$ alkyl; and
a is 0 or 1.

In another aspect, the invention provides a compound represented by Formula I wherein:
$R^1$ is H;
$R^2$ is substituted or unsubstituted heterocyle or substituted or unsubstituted aryl;
$R^3$ is substituted or unsubstituted heterocyle or substituted or unsubstituted aryl;
$R^4$ is H;
$R^5$ is H;
$R^6$ is H;
$R^7$ is H;
$R^8$ is H;
$R^9$ is H;
$R^{10}$ is H;
X is

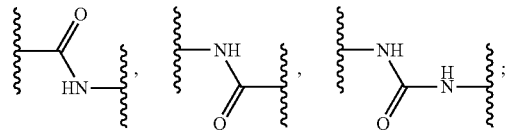 [SMILES: *NC(*)=O ; *NC(*)=O ; *NC(=O)N*]

Y is N;
W is $CR^{12}$;
$R^{12}$ is hydrogen or $C(O)OR^{17}$;
$R^{17}$ is H or substituted or unsubstituted $C_{1-8}$ alkyl; and
a is 0 or 1.

In another aspect, the invention provides a compound represented by Formula I wherein:
$R^1$ is H;
$R^2$ is substituted or unsubstituted aryl;
$R^3$ is substituted or unsubstituted aryl;
$R^4$ is H;
$R^5$ is H;
$R^6$ is H;
$R^7$ is H;
$R^8$ is H;

$R^9$ is H;
$R^{10}$ is H;
X is

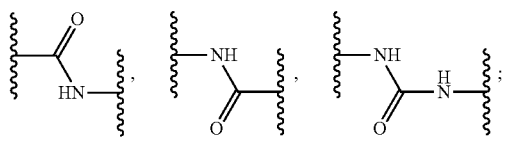

Y is N;
W is $CR^{12}$;
$R^{12}$ is hydrogen or $C(O)OR^{17}$;
$R^{17}$ is H or substituted or unsubstituted $C_{1-8}$ alkyl; and
a is 1.

The term "alkyl", as used herein, refers to saturated, monovalent or divalent hydrocarbon moieties having linear or branched moieties or combinations thereof and containing 1 to 12 carbon atoms. One methylene (—$CH_2$—) group, of the alkyl group can be replaced by oxygen, sulfur, sulfoxide, nitrogen, carbonyl, carboxyl, sulfonyl, sulfate, sulfonate, amide, sulfonamide, by a divalent $C_{3-8}$ cycloalkyl, by a divalent heterocycle, or by a divalent aryl group. Alkyl groups can have one or more chiral centers. Alkyl groups can be independently substituted by halogen atoms, hydroxyl groups, cycloalkyl groups, amino groups, heterocyclic groups, aryl groups, carboxylic acid groups, phosphonic acid groups, sulphonic acid groups, phosphoric acid groups, nitro groups, amide groups, sulfonamide groups, ester groups, ketone groups.

The term "cycloalkyl", as used herein, refers to a monovalent or divalent group of 3 to 8 carbon atoms derived from a saturated cyclic hydrocarbon. Cycloalkyl groups can be monocyclic or polycyclic. Cycloalkyl can be independently substituted by halogen atoms, sulfonyl $C_{1-8}$ alkyl groups, sulfoxide $C_{1-8}$ alkyl groups, sulfonamide groups, nitro groups, cyano groups, —$OC_{1-8}$ alkyl groups, —$SC_{1-8}$ alkyl groups, —$C_{1-8}$ alkyl groups, —$C_{2-6}$ alkenyl groups, —$C_{2-6}$ alkynyl groups, ketone groups, alkylamino groups, amide groups, amino groups, aryl groups, $C_{3-8}$ cycloalkyl groups or hydroxyl groups.

The term "cycloalkenyl", as used herein, refers to a monovalent or divalent group of 3 to 8 carbon atoms derived from a saturated cycloalkyl having at least one double bond. Cycloalkenyl groups can be monocyclic or polycyclic. Cycloalkenyl groups can be independently substituted by halogen atoms, sulfonyl groups, sulfoxide groups, nitro groups, cyano groups, —$OC_{1-6}$ alkyl groups, —$SC_{1-6}$ alkyl groups, —$C_{1-6}$ alkyl groups, —$C_{2-6}$ alkenyl groups, —$C_{2-6}$ alkynyl groups, ketone groups, alkylamino groups, amide groups, amino groups, aryl groups, $C_{3-8}$ cycloalkyl groups or hydroxyl groups.

The term "halogen", as used herein, refers to an atom of chlorine, bromine, fluorine, iodine.

The term "alkenyl", as used herein, refers to a monovalent or divalent hydrocarbon moiety having 2 to 6 carbon atoms, derived from a saturated alkyl, having at least one double bond. One methylene (—$CH_2$—) group, of the alkenyl can be replaced by oxygen, sulfur, sulfoxide, nitrogen, carbonyl, carboxyl, sulfonyl, sulfate, sulfonate, amide, sulfonamide, by a divalent $C_{3-8}$ cycloalkyl, by a divalent heterocycle, or by a divalent aryl group. $C_{2-6}$ alkenyl can be in the E or Z configuration. Alkenyl groups can be substituted by alkyl groups, as defined above or by halogen atoms.

The term "alkynyl", as used herein, refers to a monovalent or divalent hydrocarbon moiety having 2 to 6 carbon atoms, derived from a saturated alkyl, having at least one triple bond. One methylene (—$CH_2$—) group, of the alkynyl can be replaced by oxygen, sulfur, sulfoxide, nitrogen, carbonyl, carboxyl, sulfonyl, sulfate, sulfonate, amide, sulfonamide, by a divalent $C_{3-8}$ cycloalkyl, by a divalent heterocycle, or by a divalent aryl group. Alkynyl groups can be substituted by alkyl groups, as defined above, or by halogen atoms.

The term "heterocycle" as used herein, refers to a 3 to 10 membered ring, which can be aromatic or non-aromatic, saturated or unsaturated, containing at least one heteroatom selected form oxygen, nitrogen, sulfur, or combinations of at least two thereof, interrupting the carbocyclic ring structure. The heterocyclic ring can be interrupted by a C=O; the S and N heteroatoms can be oxidized. Heterocycles can be monocyclic or polycyclic. Heterocyclic ring moieties can be substituted by halogen atoms, sulfonyl groups, sulfoxide groups, nitro groups, cyano groups, —$OC_{1-6}$ alkyl groups, —$SC_{1-6}$ alkyl groups, —$C_{1-8}$ alkyl groups, —$C_{2-6}$ alkenyl groups, —$C_{2-6}$ alkynyl groups, amide groups, ketone groups, alkylamino groups, amino groups, aryl groups, ester groups, ketone groups, carboxylic acid groups, $C_{3-8}$ cycloalkyl groups or hydroxyl groups. Heterocyclic ring moieties in $R^2$ can be meta or para substituted by X. Heterocyclic ring moieties groups in $R^2$ are meta substituted by X.

The term "aryl" as used herein, refers to an organic moiety derived from an aromatic hydrocarbon consisting of a ring containing 6 to 10 carbon atoms, by removal of one hydrogen atom. Aryl can be substituted by halogen atoms, sulfonyl $C_{1-6}$ alkyl groups, sulfoxide $C_{1-6}$ alkyl groups, sulfonamide groups, carboxcyclic acid groups, $C_{1-6}$ alkyl carboxylates (ester) groups, amide groups, nitro groups, cyano groups, —$OC_{1-6}$ alkyl groups, —$SC_{1-6}$ alkyl groups, —$C_{1-6}$ alkyl groups, —$C_{2-6}$ alkenyl groups, —$C_{2-6}$ alkynyl groups, ketone groups, aldehydes, alkylamino groups, amino groups, aryl groups, $C_{3-8}$ cycloalkyl groups or hydroxyl groups. Aryls can be monocyclic or polycyclic. Aryl groups in $R^2$ can be meta or para substituted by X. Aryl groups in $R^2$ are meta substituted by X.

The term "hydroxyl" as used herein, represents a group of formula "—OH".

The term "carbonyl" as used herein, represents a group of formula "—C(O)—".

The term "ketone" as used herein, represents an organic compound having a carbonyl group linked to a carbon atom such as —$C(O)R^x$ wherein $R^x$ can be alkyl, aryl, cycloalkyl, cycloalkenyl, heterocycle as defined above.

The term "ester" as used herein, represents an organic compound having a carbonyl group linked to a carbon atom such as —$C(O)OR^x$ wherein $R^x$ can be alkyl, aryl, cycloalkyl, cycloalkenyl, heterocycle as defined above.

The term "amine" as used herein, represents a group of formula "—$NR^xR^y$", wherein $R^x$ and $R^y$ can be the same or independently H, alkyl, aryl, cycloalkyl, cycloalkenyl, heterocycle as defined above.

The term "carboxyl" as used herein, represents a group of formula "—C(O)O—".

The term "sulfonyl" as used herein, represents a group of formula "—$SO_2$—".

The term "sulfate" as used herein, represents a group of formula "—O—$S(O)_2$—O—".

The term "sulfonate" as used herein, represents a group of the formula "—$S(O)_2$—O—".

The term "carboxylic acid" as used herein, represents a group of formula "—C(O)OH".

The term "nitro" as used herein, represents a group of formula "—NO$_2$".

The term "cyano" as used herein, represents a group of formula "—CN".

The term "amide" as used herein, represents a group of formula "—C(O)NR$^x$R$^y$," or "NR$^x$R$^y$C(O)—" wherein R$^x$ and R$^y$ can be the same or independently H, alkyl, aryl, cycloalkyl, cycloalkenyl, heterocycle as defined above.

The term "sulfonamide" as used herein, represents a group of formula "—S(O)$_2$NR$^x$R$^y$" wherein R$^x$ and R$^y$ can be the same or independently H, alkyl, aryl, cycloalkyl, cycloalkenyl, heterocycle as defined above.

The term "sulfoxide" as used herein, represents a group of formula "—S(O)—".

The term "phosphonic acid" as used herein, represents a group of formula "—P(O)(OH)$_2$".

The term "phosphoric acid" as used herein, represents a group of formula "—OP(O)(OH)$_2$".

The term "sulphonic acid" as used herein, represents a group of formula "—S(O)$_2$OH".

The formula "H", as used herein, represents a hydrogen atom.

The formula "O", as used herein, represents an oxygen atom.

The formula "N", as used herein, represents a nitrogen atom.

The formula "S", as used herein, represents a sulfur atom. Other defined terms are used throughout this specification:

"CV" refers to column volume
"DMAP" refers to dimethylaminopyridine
"HPLC" refers to high pressure liquid chromatography
"MTBE" refers to tert-butyl methyl ether
"PDGF" refers to platelet derived growth factor
"PDGFRβ" refers to platelet derived growth factor receptor beta
"PTKs" refers to protein tyrosine kinase
"RTKs" refers to receptor tyrosine kinase
"rt" refers to room temperature
"VEGF" refers to vascular endothelial growth factor
"VEGFR" refers to vascular endothelial growth factor receptor Compounds of the invention are tabulated in Table 1.

| Example Number | Structure | Compound Name |
|---|---|---|
| 1 | 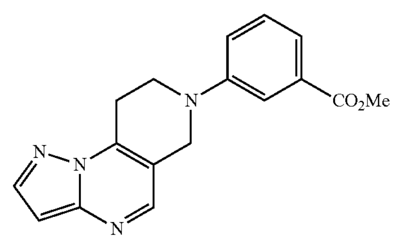 [SMILES: COC(=O)c1cccc(N2CCc3c(cnc4ccnn34)C2)c1] | Methyl 3-(8,9-dihydropyrazolo[1,5-a]pyrido[3,4-e]pyrimidin-7(6H)-yl)benzoate |
| 2 | 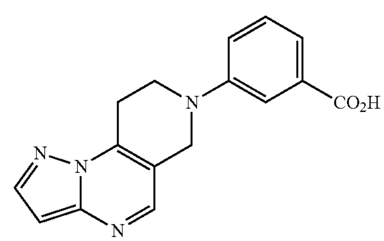 [SMILES: O=C(O)c1cccc(N2CCc3c(cnc4ccnn34)C2)c1] | 3-(8,9-dihydropyrazolo[1,5-a]pyrido[3,4-e]pyrimidin-7(6H)-yl)benzoic acid |
| 3 | 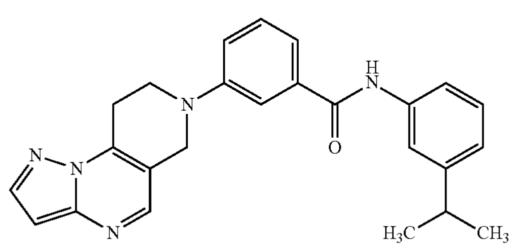 [SMILES: CC(C)c1cccc(NC(=O)c2cccc(N3CCc4c(cnc5ccnn45)C3)c2)c1] | 3-(8,9-dihydropyrazolo[1,5-a]pyrido[3,4-e]pyrimidin-7(6H)-yl)-N-(3-isopropylphenyl)benzamide |
| 4 | 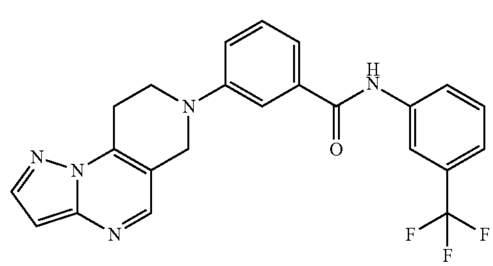 [SMILES: O=C(Nc1cccc(C(F)(F)F)c1)c1cccc(N2CCc3c(cnc4ccnn34)C2)c1] | 3-(8,9-dihydropyrazolo[1,5-a]pyrido[3,4-e]pyrimidin-7(6H)-yl)-N-[3-(trifluoromethyl)phenyl]benzamide |

-continued

| Example Number | Structure | Compound Name |
|---|---|---|
| 5 | 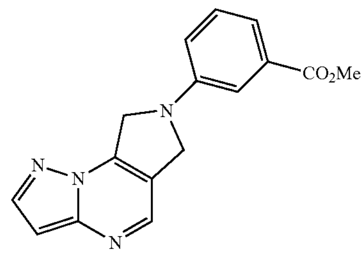 [SMILES: COC(=O)c1cccc(N2Cc3cnc4ccnn4c3C2)c1] | Methyl 3-(6,8-dihydro-7H-pyrazolo[1,5-a]pyrrolo[3,4-e]pyrimidin-7-yl)benzoate |
| 6 | 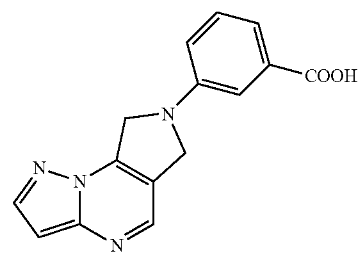 [SMILES: O=C(O)c1cccc(N2Cc3cnc4ccnn4c3C2)c1] | 3-(6,8-dihydro-7H-pyrazolo[1,5-a]pyrrolo[3,4-e]pyrimidin-7-yl)benzoic acid |
| 7 | 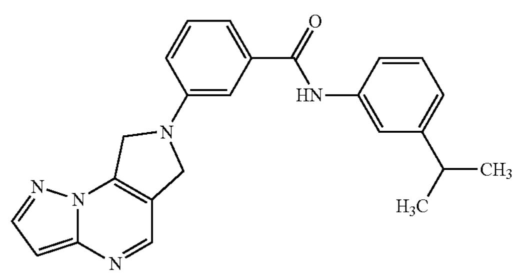 [SMILES: CC(C)c1cccc(NC(=O)c2cccc(N3Cc4cnc5ccnn5c4C3)c2)c1] | 3-(6,8-dihydro-7H-pyrazolo[1,5-a]pyrrolo[3,4-e]pyrimidin-7-yl)-N-(3-isopropylphenyl)benzamide |
| 8 | 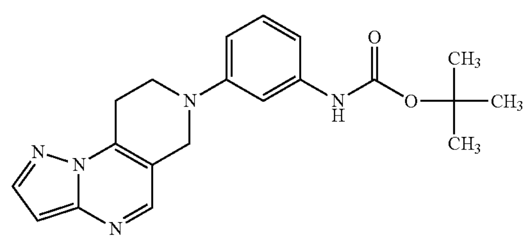 [SMILES: CC(C)(C)OC(=O)Nc1cccc(N2CCc3c(cnc4ccnn34)C2)c1] | tert-Butyl (3-(8,9-dihydropyrazolo[1,5-a]pyrido[3,4-e]pyrimidin-7(6H)-yl)phenyl)carbamate |
| 9 | 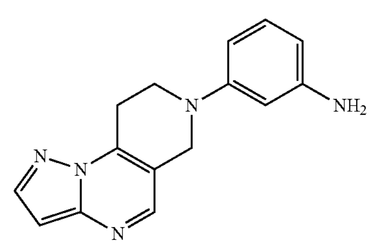 [SMILES: Nc1cccc(N2CCc3c(cnc4ccnn34)C2)c1] | 3-(8,9-Dihydropyrazolo[1,5-a]pyrido[3,4-e]pyrimidin-7(6H)-yl)benzenamine |
| 10 | 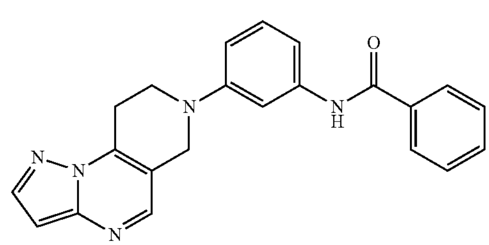 [SMILES: O=C(Nc1cccc(N2CCc3c(cnc4ccnn34)C2)c1)c1ccccc1] | N-[3-(8,9-dihydropyrazolo[1,5-a]pyrido[3,4-e]pyrimidin-7(6H)-yl)phenyl]benzamide |

-continued

| Example Number | Structure | Compound Name |
|---|---|---|
| 11 | 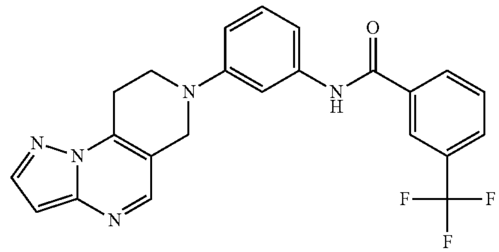 [SMILES: O=C(Nc1cccc(N2CCc3c(cnc4ccnn34)C2)c1)c1cccc(C(F)(F)F)c1] | N-[3-(8,9-dihydropyrazolo[1,5-a]pyrido[3,4-e]pyrimidin-7(6H)-yl)phenyl]-3-(trifluoromethyl)benzamid |
| 12 | 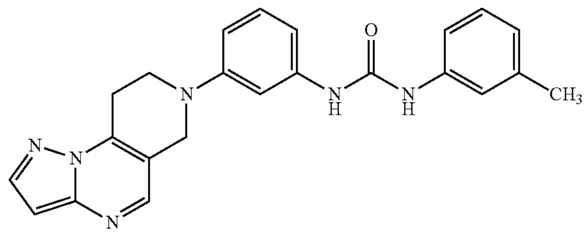 [SMILES: Cc1cccc(NC(=O)Nc2cccc(N3CCc4c(cnc5ccnn45)C3)c2)c1] | 1-[3-(8,9-dihydropyrazolo[1,5-a]pyrido[3,4-e]pyrimidin-7(6H)-yl)phenyl]-3-(3-methylphenyl)urea |
| 13 | 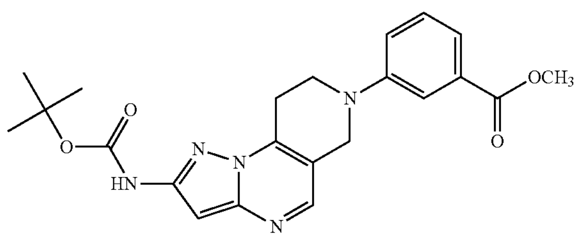 [SMILES: COC(=O)c1cccc(N2CCc3c(cnc4cc(NC(=O)OC(C)(C)C)nn34)C2)c1] | Methyl 3-(2-((tert-butoxycarbonyl)amino)-8,9-dihydropyrazolo[1,5-a]pyrido[3,4-e]pyrimidin-7(6H)-yl)benzoate |
| 14 | 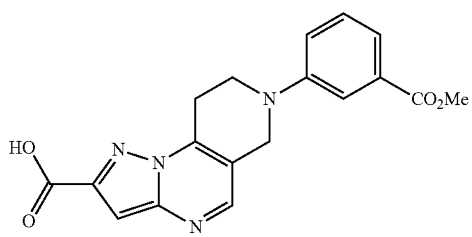 [SMILES: COC(=O)c1cccc(N2CCc3c(cnc4cc(C(=O)O)nn34)C2)c1] | 7-(3-Methoxycarbonyl)phenyl)-6,7,8,9-tetrahydropyrazolo[1,5-a]pyrido[3,4-e]pyrimidine-2-carboxylic acid |

In another embodiment, compounds of the invention are:
3-(8,9-dihydropyrazolo[1,5-a]pyrido[3,4-e]pyrimidin-7(6H)-yl)-N-(3-isopropylphenyl)benzamide;
3-(8,9-dihydropyrazolo[1,5-a]pyrido[3,4-e]pyrimidin-7(6H)-yl)-N-[3-(trifluoromethyl)phenyl]benzamide;
3-(6,8-dihydro-7H-pyrazolo[1,5-a]pyrrolo[3,4-e]pyrimidin-7-yl)-N-(3-isopropylphenyl)benzamide;
tert-Butyl (3-(8,9-dihydropyrazolo[1,5-a]pyrido[3,4-e]pyrimidin-7(6H)-yl)phenyl)carbamate;
N-[3-(8,9-dihydropyrazolo[;1,5-a]pyrido[3,4-e]pyrimidin-7(6H)-yl)phenyl]benzamide
N-[3-(8,9-dihydropyrazolo[1,5-a]pyrido[3,4-e]pyrimidin-7(6H)-yl)phenyl]-3-(trifluoromethyl)benzamide;
1-[3-(8,9-dihydropyrazolo[1,5-a]pyrido[3,4-e]pyrimidin-7(6H)-yl)phenyl]-3-(3-methylphenyl)urea.

Compounds of formula I are useful as protein kinase inhibitors. As such, compounds of formula I will be useful for treating diseases related to protein kinase signal transduction, for example, cancer, blood vessel proliferative disorders, fibrotic disorders, and neurodegenerative diseases. In particular, the compounds of the present invention are useful for treatment of mesangial cell proliferative disorders and metabolic diseases, lung carcinomas, breast carcinomas, Non Hodgkin's lymphomas, ovarian carcinoma, pancreatic cancer, malignant pleural mesothelioma, melanoma, arthritis, restenosis, hepatic cirrhosis, atherosclerosis, psoriasis, rosacea, diabetic mellitus, wound healing, inflammation and neurodegenerative diseases and preferably ophthalmic diseases, i.e. diabetic retinopathy, retinopathy of prematurity, macular edema, retinal vein occlusion, exudative or neovascular age-related macular degeneration, high-risk eyes (i.e. fellow eyes have neovascular age-related macular degeneration) with dry age-related macular degeneration, neovascular disease associated with retinal vein occlusion, neovascular disease (including choroidal neovascularization) associated with the following: pathologic myopia, pseudoxanthoma elasticum, optic nerve drusen, traumatic choroidal rupture, serous retinopathy, cystoid macular edema, diabetic retinopathy, proliferative diabetic retinopathy, diabetic macular edema, rubeosis iridis, retinopathy of prematurity, Central and branch retinal vein occlusions, inflammatory/infectious retinal, neovascularization/edema, corneal neovascularization, hyperemia related to an actively inflamed pterygia, recurrent pterygia following excisional surgery, post-excision, progressive pterygia approaching the visual axis, prophylactic therapy to prevent recurrent pterygia, of post-excision, progressive pterygia approaching the visual axis, chronic low grade hyperemia associated with pterygia, neovascular glaucoma, iris neovascularization, idiopathic etiologies, presumed ocular histoplasmosis syndrome, retinopathy of prematurity, chronic allergic conjunctivitis, ocular rosacea, blepharoconjunctivitis, recurrent episcleritis, keratoconjunctivitis sicca, ocular graft vs host disease, etc.

The fibrotic disorder is selected from the group consisting of hepatic cirrhosis and atherosclerosis.

The mesangial cell proliferative disorder is selected from the group consisting of glomerulonephritis, diabetic nephropathy, malignant nephrosclerosis, thrombotic microangiopathy syndromes, transplant rejection and glomerulopathies.

The metabolic disease is selected from the group consisting of psoriasis, diabetes mellitus, wound healing, inflammation and neurodegenerative diseases. The blood vessel proliferative disorder is selected from the group consisting of diabetic retinopathy, exudative age-related macular degeneration, retinopathy of prematurity, pterigium, rosacea, arthritis and restenosis.

Some compounds of Formula I and some of their intermediates may have at least one asymmetric center in their structure. This asymmetric center may be present in an R or S configuration, said R and S notation is used in correspondence with the rules described in Pure Applied Chem. (1976), 45, 11-13.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I are able to form.

The acid addition salt form of a compound of Formula I that occurs in its free form as a base can be obtained by treating the free base with an appropriate acid such as an inorganic acid, for example, hydrochloric acid, hydrobromic acid, sulfuric acid, phosphoric acid, nitric acid and the like; or an organic acid such as for example, acetic acid, hydroxyacetic acid, propanoic acid, lactic acid, pyruvic acid, malonic acid, fumaric acid, maleic acid, oxalic acid, tartaric acid, succinic acid, malic acid, ascorbic acid, benzoic acid, tannic acid, pamoic acid, citric acid, methylsulfonic acid, ethanesulfonic acid, benzenesulfonic acid, formic and the like (Handbook of Pharmaceutical Salts, P. Heinrich Stahl & Camille G. Wermuth (Eds), Verlag Helvetica Chimica Acta-Zurich, 2002, 329-345).

The base addition salt form of a compound of Formula I that occurs in its acid form can be obtained by treating the acid with an appropriate base such as an inorganic base, for example, sodium hydroxide, magnesium hydroxide, potassium hydroxide, calcium hydroxide, ammonia and the like; or an organic base such as for example, L-Arginine, ethanolamine, betaine, benzathine, morpholine and the like. (Handbook of Pharmaceutical Salts, P. Heinrich Stahl & Camille G. Wermuth (Eds), Verlag Helvetica Chimica Acta-Zurich, 2002, 329-345).

Compounds of Formula I and their salts can be in the form of a solvate, which is included within the scope of the present invention. Such solvates include for example hydrates, alcoholates and the like.

With respect to the present invention reference to a compound or compounds, is intended to encompass that compound in each of its possible isomeric forms and mixtures thereof unless the particular isomeric form is referred to specifically.

Compounds according to the present invention may exist in different polymorphic forms. Although not explicitly indicated in the above formula, such forms are intended to be included within the scope of the present invention.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back to the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Pharmaceutical compositions containing invention compounds may be in a form suitable for topical use, for example, as oily suspensions, as solutions or suspensions in aqueous liquids or nonaqueous liquids, or as oil-in-water or water-in-oil liquid emulsions. Pharmaceutical compositions may be prepared by combining a therapeutically effective amount of at least one compound according to the present invention, or a pharmaceutically acceptable salt thereof, as an active ingredient with conventional ophthalmically acceptable pharmaceutical excipients and by preparation of unit dosage suitable for topical ocular use. The therapeutically efficient amount typically is between about 0.0001 and about 5% (w/v), preferably about 0.001 to about 2.0% (w/v) in liquid formulations.

For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional pharmaceutically acceptable preservatives, stabilizers and surfactants. Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar manner an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, although other chelating agents may also be used in place of or in conjunction with it.

The ingredients are usually used in the following amounts:
Ingredient Amount (% w/v)
active ingredient about 0.001-5
preservative 0-0.10
vehicle 0-40
tonicity adjustor 0-10
buffer 0.01-10
pH adjustor q.s. pH 4.5-7.8
antioxidant as needed
surfactant as needed
purified water to make 100%

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate application to the eye. Containers suitable for dropwise application are usually made of suitable inert, non-toxic plastic material, and generally contain between about 0.5 and about 15 ml solution. One package may contain one or more unit doses. Especially preservative-free solutions are often formulated in non-resealable containers containing up to about ten, preferably up to about five units doses, where a typical unit dose is from one to about 8 drops, preferably one to about 3 drops. The volume of one drop usually is about 20-35 µl.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

The compounds of the invention may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The present invention is further directed to pharmaceutical compositions comprising a pharmaceutically effective amount of one or more of the above-described compounds and a pharmaceutically acceptable carrier or excipient, wherein said compositions are effective for treating the above diseases and conditions; especially ophthalmic diseases and conditions. Such a composition is believed to modulate signal transduction by a tyrosine kinase, either by inhibition of catalytic activity, affinity to ATP or ability to interact with a substrate.

More particularly, the compositions of the present invention may be included in methods for treating diseases comprising proliferation, fibrotic or metabolic disorders, for example cancer, fibrosis, psoriasis, rosacea, atherosclerosis, arthritis, and other disorders related to abnormal vasculogenesis and/or angiogenesis, such as exudative age related macular degeneration and diabetic retinopathy.

The present invention concerns also processes for preparing the compounds of Formula I. The compounds of formula I according to the invention can be prepared analogously to conventional methods as understood by the person skilled in the art of synthetic organic chemistry. Synthetic Schemes set forth below, illustrate how the compounds according to the invention can be made.

Scheme 1

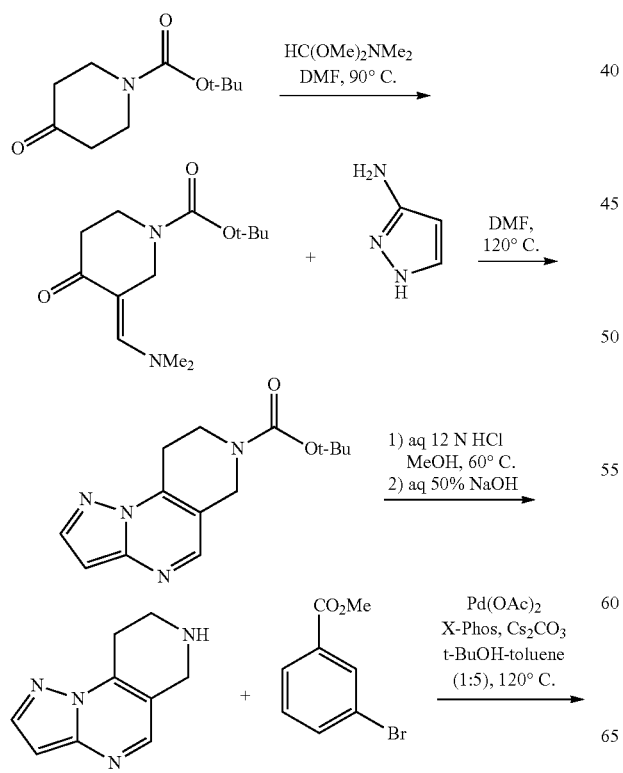

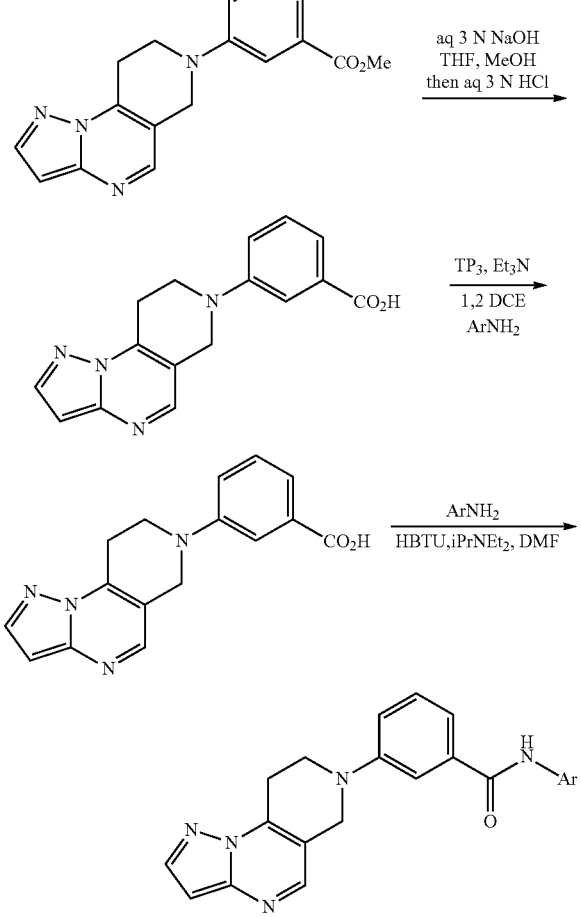

Scheme 2

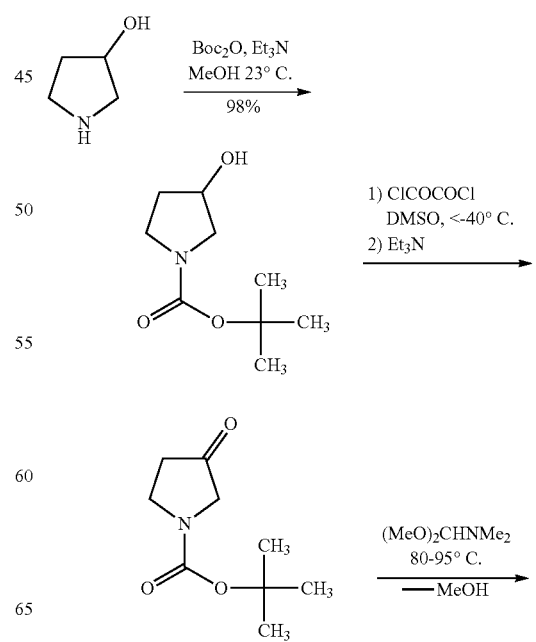

25
-continued
26
-continued
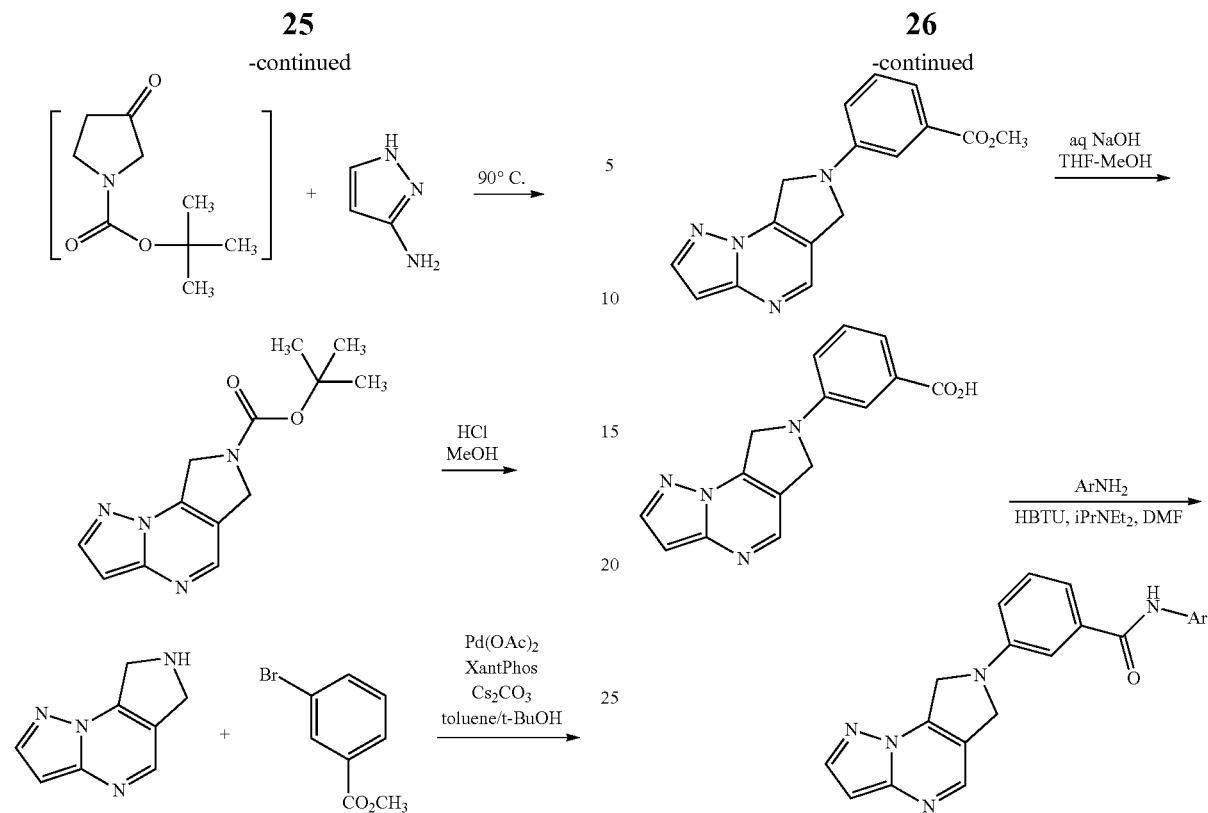
Scheme 3
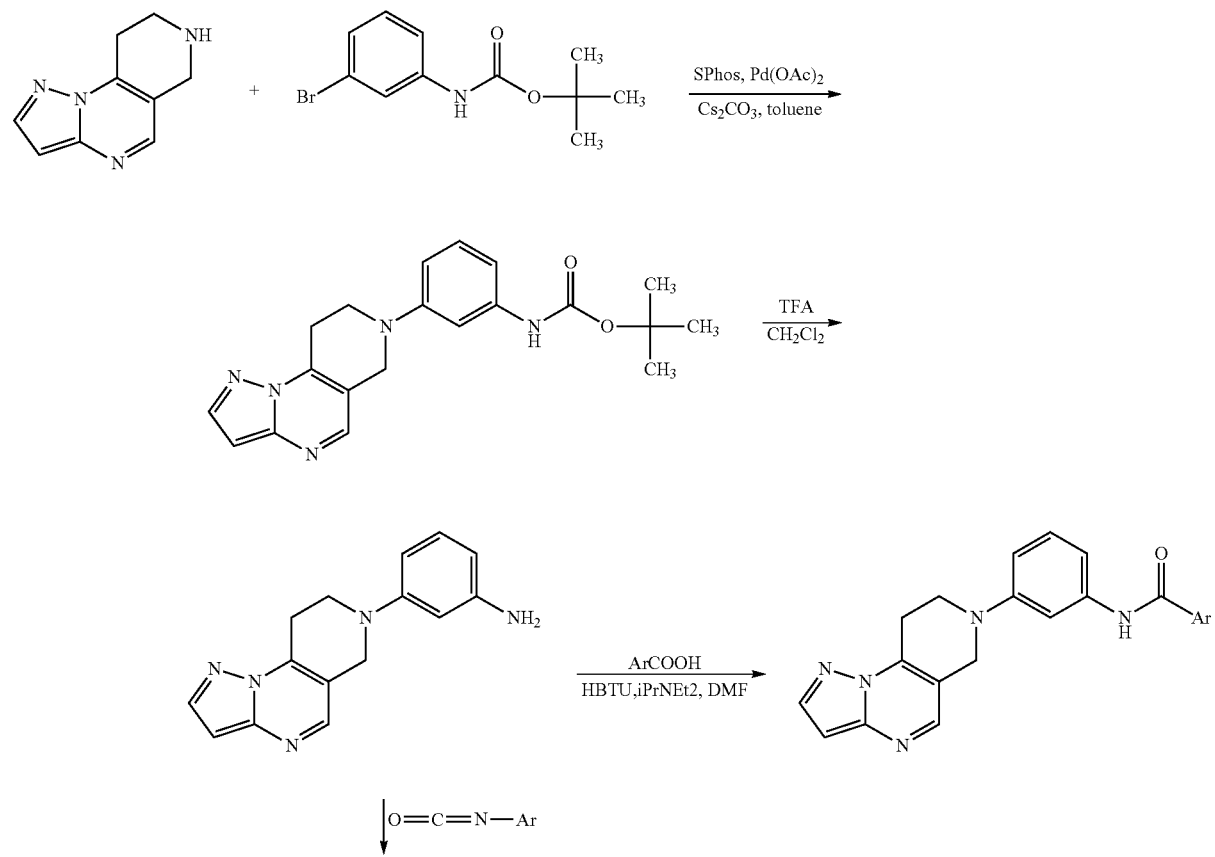

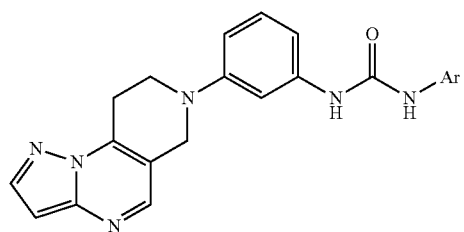
Scheme 4
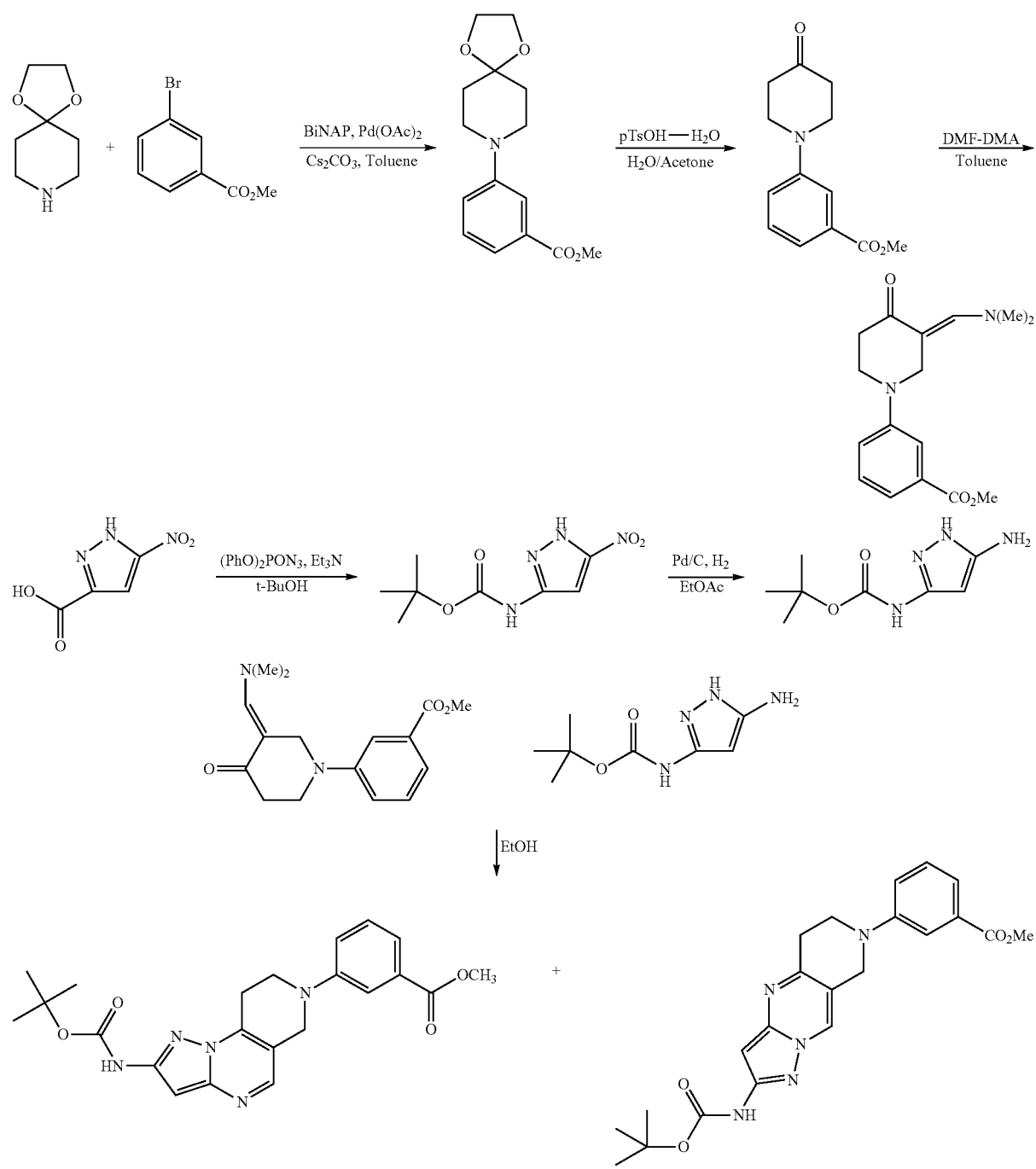

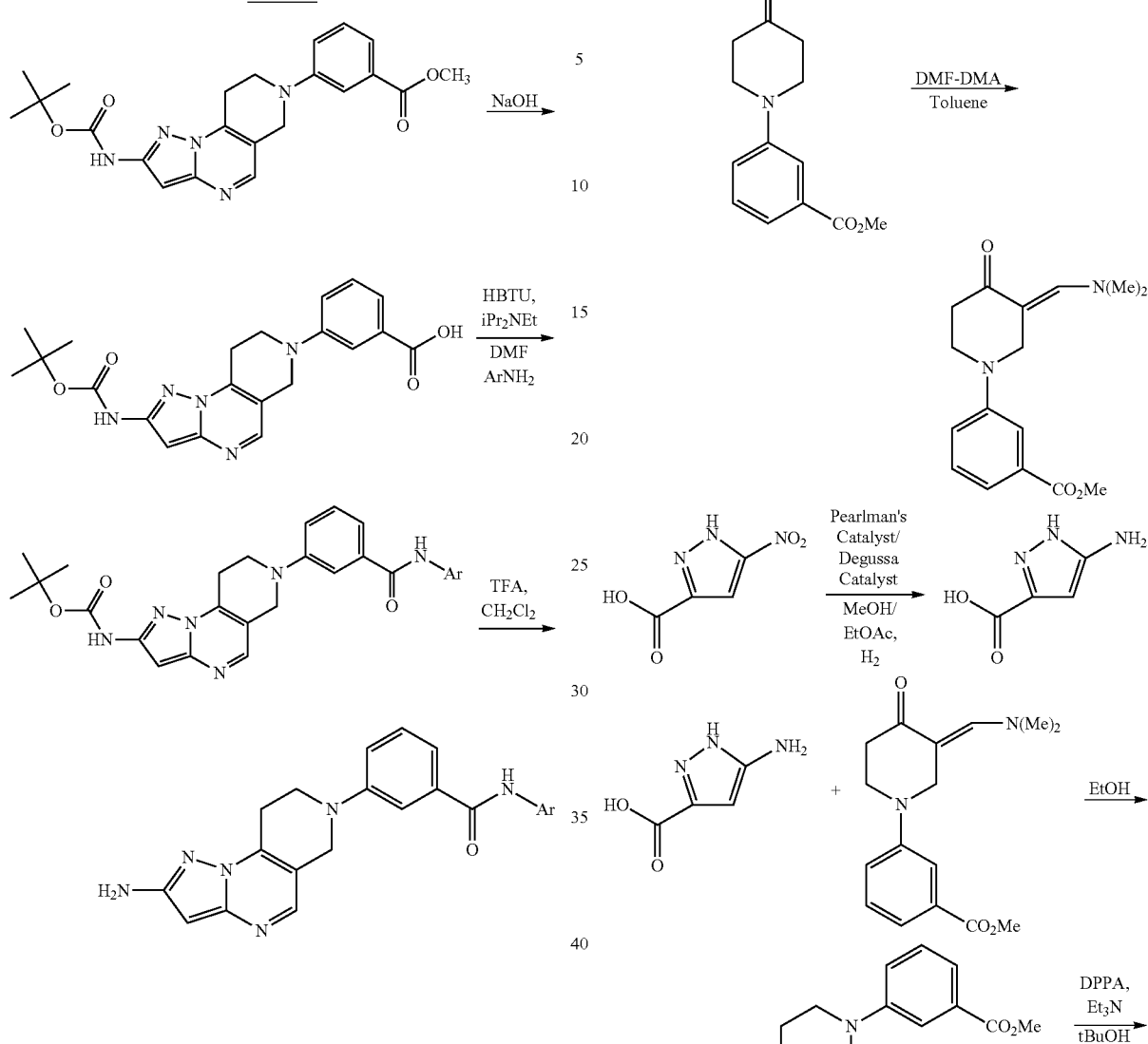

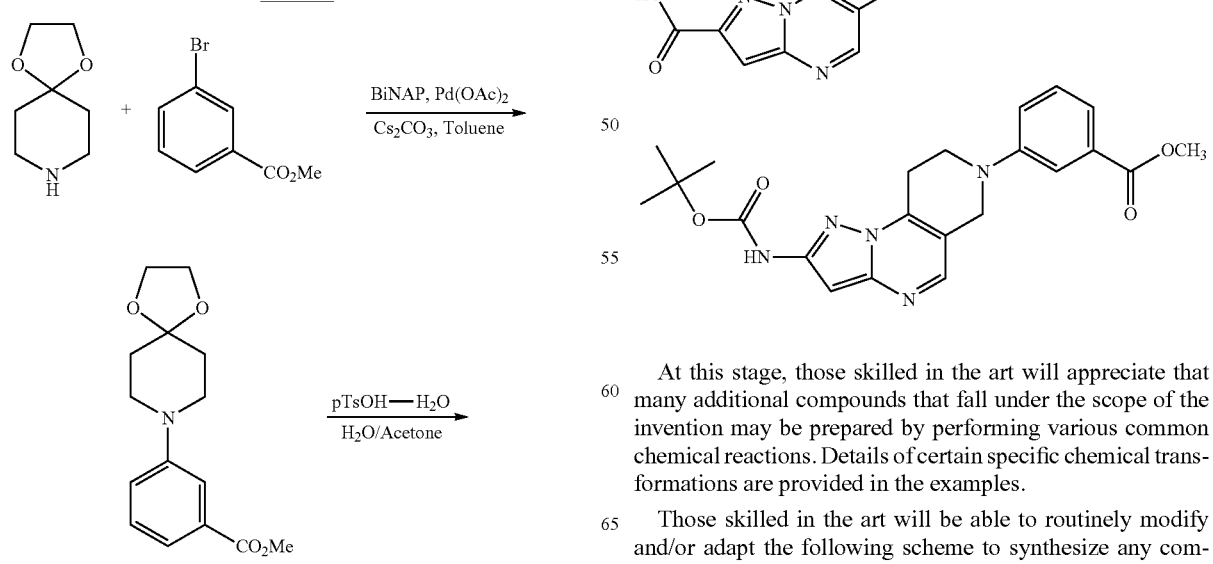

At this stage, those skilled in the art will appreciate that many additional compounds that fall under the scope of the invention may be prepared by performing various common chemical reactions. Details of certain specific chemical transformations are provided in the examples.

Those skilled in the art will be able to routinely modify and/or adapt the following scheme to synthesize any compounds of the invention covered by Formula I.

The present invention is not to be limited in scope by the exemplified embodiments which are intended as illustrations of single aspects of the invention only. Indeed, various modifications of the invention in addition to those described herein will become apparent to those skilled in the art from the foregoing description.

DETAILED DESCRIPTION OF THE INVENTION

The present invention relates to a method of regulating, modulating or inhibiting tyrosine kinases, whether of the receptor or non-receptor class, for the prevention and/or treatment of disorders related to unregulated tyrosine kinase signal transduction, including cell growth, metabolic, and blood vessel proliferative disorders, which comprises administering a pharmaceutical composition comprising a therapeutically effective amount of at least one kinase inhibitor as described herein.

In another aspect, the invention provides the use of at least one kinase inhibitor for the manufacture of a medicament for the treatment of a disease or a condition mediated by tyrosine kinases in a mammal.

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2H$ (or D) in place of hydrogen $^1H$ (or H) or use of $^{13}C$ enriched material in place of $^{12}C$ and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

The following examples are for illustrative purposes only and are not intended, nor should they be construed as limiting the invention in any manner. Those skilled in the art will appreciate that variations and modifications of the following examples can be made without exceeding the spirit or scope of the invention.

As will be evident to those skilled in the art, individual isomeric forms can be obtained by separation of mixtures thereof in conventional manner. For example, in the case of diasteroisomeric isomers, chromatographic separation may be employed.

Compound names were generated with ACDLabs version 12.5. Some of the intermediate and reagent names used in the examples were generated with software such as Chem Bio Draw Ultra version 12.0 or Auto Nom 2000 from MDL ISIS Draw 2.5 SP1.

In general, characterization of the compounds is performed according to the following methods; NMR spectra are recorded on 300 or 600 MHz Varian and acquired at room temperature. Chemical shifts are given in ppm referenced either to internal TMS or to the solvent signal.

All the reagents, solvents, catalysts for which the synthesis is not described are purchased from chemical vendors such as Sigma Aldrich, Fluka, Bio-Blocks, Combi-blocks, TCI, VWR, Lancaster, Oakwood, Trans World Chemical, Alfa, Fisher, Maybridge, Frontier, Matrix, Ukrorgsynth, Toronto, Ryan Scientific, SiliCycle, Anaspec, Syn Chem, Chem-Impex, MIC-scientific, Ltd; however some known intermediates, were prepared according to published procedures.

Usually the compounds of the invention were purified by medium pressure liquid chromatography, unless noted otherwise.

Preparation 1

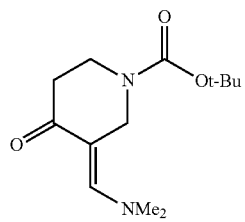

(E)-tert-butyl 3-((dimethylamino)methylene)-4-oxopiperidine-1-carboxylate

A 500 mL round-bottomed flask was equipped with a magnetic stirrer and stir bar, heating bath, air condenser, nitrogen inlet. The flask was charged with 1-t-butoxycarbonylpiperid-4-one (50 g, 250 mmol) and N,N-dimethylformamide dimethyl acetal (36.5 mL, 32.5 g, 273 mmol). The stirred solution was heated to 90° C. under nitrogen for 20 hours. Assay of an aliquot by HPLC showed that the reaction was nearly complete. After cooling, the batch was concentrated in vacuo (bath temperature 54° C.). The residue was partitioned between saturated aqueous sodium chloride (1 L) and ethyl acetate (1 L). The separated organic layer was dried over anhydrous sodium sulfate (200 g), filtered, and concentrated under reduced pressure to give the title compound as an amber oil (68.3 g, 107% yield).

Preparation 2

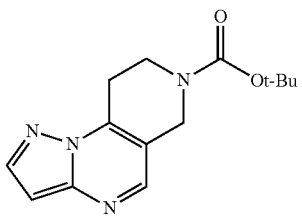

tert-butyl 8,9-dihydropyrazolo[1,5-a]pyrido[3,4-e]pyrimidine-7(6H)-carboxylate

A 1 L, three-necked round-bottomed flask was equipped with a magnetic stirrer and stir bar, air condenser, thermocouple, heating bath and nitrogen inlet. To a solution of (E)-tert-butyl 3-((dimethylamino)methylene)-4-oxopiperidine-1-carboxylate (66.8 g, 250 mmol) in N,N-dimethylformamide (600 mL) was added 3-aminopyrazole (22.8 g, 274 mmol). The batch was stirred at 120° C. for 20 hours. An aliquot analyzed by HPLC at 18 hours showed starting material remaining. The cooled mixture was concentrated under reduced pressure (58° C. bath), and the residue was taken-up in diethyl ether (1 L); after washing with saturated aqueous sodium chloride (1 L), the organic layer was dried over anhydrous sodium sulfate (210 g). Filtration and concentration in vacuo afforded crude product (64.5 g). The crude product was dissolved in ethyl acetate (100 mL) and loaded onto a 1500 g KP-Sil SNAP cartridge pre-equilibrated with 20% by volume ethyl acetate in hexanes (3 CV). Gradient elution was run with 20% to 40% by volume ethyl acetate in hexanes (9 CV), followed by isocratic elution with 40% by volume ethyl acetate in hexanes (9 CV), and collecting four fractions. Fraction 1 (10-14 L of eluent), fraction 2 (14-15.1 L of eluent), and fraction 3 (15.1-17 L of eluent) contained pure product and were combined. Fraction 4 (17-20 L of eluent) provided the title compound (6.15 g) of 92% pure product after concentration in vacuo. This impure material was re-purified as above, using a 100 g KP-Sil cartridge; pure fractions were pooled with those previously obtained. Removal of solvent under reduced pressure afforded the title compound (48.4 g, 71% yield).

Preparation 3

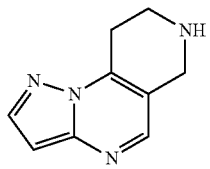

6,7,8,9-Tetrahydropyrazolo[1,5-a]pyrido[3,4-e]pyrimidine

A 1 L, three-necked, round-bottomed flask was equipped with a magnetic stirrer and stir bar, 250 mL addition funnel, heating bath, thermocouple, condenser, nitrogen inlet and ice water bath. To a stirred solution of tert-butyl 8,9-dihydropyrazolo[1,5-a]pyrido[3,4-e]pyrimidine-7(6H)-carboxylate (41.9 g) in methanol (300 mL) at 40° C. was added aqueous 12 N hydrochloric acid (112 mL) via the addition funnel (exotherm to 60° C. and gas evolution). Analysis of an aliquot by HPLC after 23 hours showed the reaction to be complete. The batch was cooled with an external ice bath while aqueous 50% by weight sodium hydroxide (83 mL) was added via the addition funnel to bring the pH>9. The mixture was concentrated in vacuo by removing ~350 mL of distillate. The residue was diluted with of water (100 mL) and saturated aqueous sodium chloride (200 mL). The batch was extracted with dichloromethane (10×100 mL), and the combined organic extracts were dried over anhydrous sodium sulfate (250 g), filtered, and concentrated in vacuo to give the title compound (26.2 g, 98% yield).

Example 1

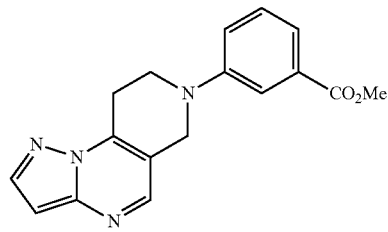

Methyl 3-(8,9-dihydropyrazolo[1,5-a]pyrido[3,4-e]pyrimidin-7(6H)-yl)benzoate

A 500 mL heavy-walled vessel with threaded stopper was equipped with a magnetic stirrer and stir bar and heating bath. The vessel was charged under a nitrogen blanket with palladium(II) acetate (700 mg, 3.12 mmol), 2-(dicyclohexylphosphino)-2',4',6'-tri-i-propyl-1,1'-biphenyl (1.5 g, 3.15 mmol), cesium carbonate (10.2 g, 31 mmol), and degassed toluene-t-BuOH 5:1 (50 mL). This mixture was stirred under nitrogen for 5 minutes. A degassed solution of 6,7,8,9-tetrahydropyrazolo[1,5-a]pyrido[3,4-e]pyrimidine (5 g, 28.7 mmol) and methyl 3-bromobenzoate (12.9 g, 60 mmol) in toluene-t-BuOH 5:1 (250 mL) was quickly added. The vessel was sealed under nitrogen and heated at 120° C. for 18 hours. The cooled batch was filtered through a pad of Celite® (14 g) layered upon 230-400 mesh silica gel (32 g), completing the transfer through the pad with ethyl acetate (300 mL). The filtrate and rinse were concentrated in vacuo to provide 14 g of dark oil. This material was purified on a Biotage® unit (340 g SNAP KP-Sil cartridge equilibrated with 3 CV of 20% by volume ethyl acetate in hexane). Gradient elution was performed with 20% by volume ethyl acetate in hexane (1 CV), 20-50% by volume ethyl acetate in hexanes (3 CV), 50% by volume ethyl acetate in hexanes (10 CV), 50-60% by volume ethyl acetate in hexanes (2 CV), and 60-70% by volume ethyl acetate in hexane (2 CV). Pooling the clean fractions (12-16 CV) and concentration under reduced pressure afforded the title compound (2.25 g, 25% yield) of 99% purity.

Example 2

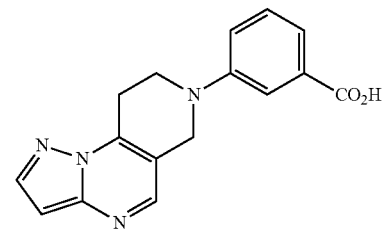

3-(8,9-dihydropyrazolo[1,5-a]pyrido[3,4-e]pyrimidin-7(6H)-yl)benzoic acid

A 250 mL, single-necked, round-bottomed flask was equipped with a magnetic stirrer and stir bar, heating bath, condenser and nitrogen inlet. The flask was charged with methyl 3-(8,9-dihydropyrazolo[1,5-a]pyrido[3,4-e]pyrimidin-7(6H)-yl)benzoate (2.9 g, 9.4 mmol), tetrahydrofuran (70 mL), methanol (50 mL), and aqueous 3 N sodium hydroxide (15 mL). The reaction mixture was then heated with stirring to 45° C. and kept at that temperature for 4 hours. An aliquot showed that hydrolysis was complete. After cooling, the batch was acidified to pH 6 with aqueous 3 N hydrochloric acid (21 mL). Solvent removal in vacuo provided a yellowish solid (6.2 g), which was triturated in boiling methanol (200 mL) and filtered through a fritted glass funnel. The filtrate was concentrated under reduced pressure to afford the title compound (3.9 g).

Example 3

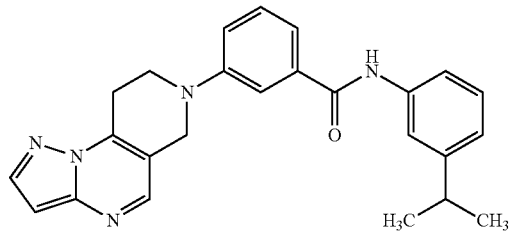 [SMILES: CC(C)c1cccc(NC(=O)c2cccc(N3CCc4c(cnc5ccnn45)C3)c2)c1]

3-(8,9-dihydropyrazolo[1,5-a]pyrido[3,4-e]pyrimidin-7(6H)-yl)-N-(3-isopropylphenyl)benzamide To a mixture of 3-(8,9-dihydropyrazolo[1,5-a]pyrido[3,4-e]pyrimidin-7(6H)-yl)benzoic acid (0.20 mmol, 59 mg), triethylamine (0.40 mmol, 0.056 mL), and catalytic DMAP in 2.0 mL 1,2-dichloroethane at rt was added propylphosphonic anhydride solution (50 wt % in EtOAc, 0.24 mmol, 0.143 mL). After 10 min at rt, 3-isopropylaniline (0.30 mmol, 0.042 mL) was added and the reaction stirred at rt for 1 hour. The reaction was quenched into dilute aqueous Na$_2$CO$_3$ solution, extracted into EtOAc, the EtOAc layer washed with H$_2$O, dilute aqueous Na$_2$CO$_3$ solution, brine, dried with anhydrous Na$_2$SO$_4$ and rotary evaporated. This material was chromatographed eluting with CHCl$_3$/EtOAc and then recrystallized from EtOAc/hexane to give the title compound as a light yellow solid (16 mg, 20%).

$^1$H NMR (Acetone-d6) δ: 9.41 (br. s., 1H), 8.51 (s, 1H), 8.12 (d, J=2.1 Hz, 1H), 7.71-7.75 (m, 2H), 7.66-7.71 (m, 1H), 7.33-7.48 (m, 3H), 7.27 (t, J=7.8 Hz, 1H), 7.01 (d, J=7.6 Hz, 1H), 6.66 (d, J=2.3 Hz, 1H), 4.63 (s, 2H), 3.93 (t, J=5.9 Hz, 2H), 3.35-3.42 (m, 2H), 2.91 (spt, J=7.0 Hz, 1H), 1.25 (d, J=7.0 Hz, 6H).

Example 4

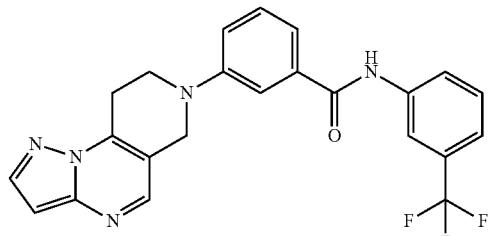

3-(8,9-dihydropyrazolo[1,5-a]pyrido[3,4-e]pyrimidin-7(6H)-yl)-N-[3-(trifluoromethyl)phenyl]benzamide To a mixture of 3-(8,9-dihydropyrazolo[1,5-a]pyrido[3,4-e]pyrimidin-7(6H)-yl)benzoic acid (0.20 mmol, 59 mg), triethylamine (0.40 mmol, 0.056 mL), and catalytic DMAP in 2.0 mL 1,2-dichloroethane at rt was added propylphosphonic anhydride solution (50 wt % in EtOAc, 0.24 mmol, 0.143 mL). After 10 min at rt, 3-(trifluoromethyl)aniline (0.30 mmol, 0.042 mL) was added and the reaction stirred at rt for 20 hours. The reaction was quenched into dilute aqueous Na$_2$CO$_3$ solution, extracted into EtOAc, the EtOAc layer washed with H$_2$O, dilute aqueous Na$_2$CO$_3$ solution, brine, dried with anhydrous Na$_2$SO$_4$ and rotary evaporated. This material was chromatographed eluting with CHCl$_3$/EtOAc and then recrystallized from EtOAc/hexane to give the title compound as a light yellow solid (20 mg, 23%).

$^1$H NMR (Acetone-d6) δ: 9.76 (br. s., 1H), 8.50 (s, 1H), 8.32 (s, 1H), 8.11-8.13 (m, 1H), 8.08 (d, J=8.5 Hz, 1H), 7.77 (s, 1H), 7.60 (t, J=8.1 Hz, 1H), 7.37-7.50 (m, 4H), 6.65-6.67 (m, 1H), 4.64 (s, 2H), 3.94 (t, J=5.9 Hz, 2H), 3.35-3.42 (m, 2H)

Preparation 4

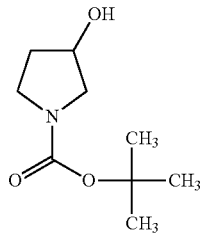

tert-butyl 3-hydroxypyrrolidine-1-carboxylate

A 3 L, four-necked, round-bottomed flask, was equipped with a mechanical stirrer, 1 L addition funnel, K-type thermocouple, cooling bath and nitrogen inlet. A stirred solution of DL-pyrrolidinol (140.0 g, 1.61 mol), triethylamine (228 g, 314 mL, 2.25 mol), and MeOH (1500 mL) was aged under nitrogen at 15-20° C. in a cold water bath for 20 minutes. Neat di-t-butyl dicarbonate (528.0 g, 2.42 mol) was added dropwise, adding ice to the cooling bath to maintain an internal temperature below 30° C. After the addition was complete, the batch was stirred at 15-25° C. overnight. The mixture was concentrated under reduced pressure to a residue, which was purified by passage through silica gel (230-400 mesh, 1000 g) packed with 50% by volume ethyl acetate-hexane (2000 mL). The product was eluted with ethyl acetate (8000 mL), taking 250 mL fractions. Pure fractions were pooled and concentrated in vacuo to give the title compound as an off white solid (294 g, 98% yield).

Preparation 5

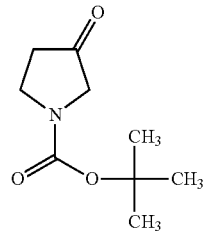

tert-butyl 3-oxopyrrolidine-1-carboxylate

A 3 L, four-necked round-bottomed flask was equipped with a mechanical stirrer, 500 mL addition funnel, cooling bath, K-type thermocouple and a nitrogen inlet. The flask was charged with oxalyl chloride (149.8 g, 1.18 mol) and dichloromethane (700 mL) and cooled to −69° C. The stirred solution was treated drop-wise with a solution of dimethyl sulfoxide (99.2 g, 1.27 mol) in dichloromethane (150 mL), maintaining an internal temperature below −60° C. (copious gas generation). This mixture was briefly warmed to −40° C. before cooling to −69° C. A solution of tert-butyl 3-hydroxypyrrolidine-1-carboxylate (100.0 g, 0.534 mol) in dichloromethane (350 mL) was charged drop-wise to the batch, maintaining an internal temperature below −60° C. The stirred reaction mixture was allowed to age at −50° C. for 30 minutes and cooled to −69° C. Neat triethylamine (270 g, 2.67 mol) was added drop-wise, while maintaining an internal temperature below −60° C. Upon completion of the addition, the batch was allowed to age for 30 minutes at −60° C., before warming to ambient temperature over about 1 hour. The reaction mixture was washed with 5% mass to volume aqueous citric acid solution (2×180 mL). The separated aqueous layer was extracted with dichloromethane (2×200 mL), and the combined the organic phases were dried over anhydrous sodium sulfate (30 g), filtered and concentrated under reduced pressure. The title compound was obtained as a dark brown oily product (95.0 g, 96% yield) and was used in the next step without further purification.

Preparation 6

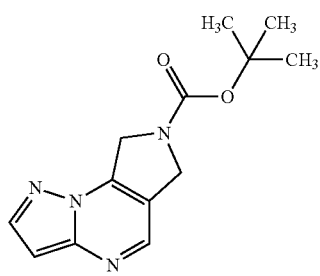

tert-butyl 6,8-dihydro-7H-pyrazolo[1,5-a]pyrrolo[3,4-e]pyrimidine-7-carboxylate

A 125 mL round-bottomed flask was equipped with a magnetic stirrer and stir bar, distillation head, heating bath, thermocouple and nitrogen inlet. The flask was charged with tert-butyl 3-oxopyrrolidine-1-carboxylate (17 g, 91.9 mmol) and N,N-dimethylformamide dimethyl acetal (14.4 g, 120.8 mmol). The stirred mixture was heated to 95° C. over 2.33 hours, while the methanol formed was distilled-off. During this operation, the internal temperature was at 78° C. and later rose to 95° C. after 1 hour (matching external heating bath temperature). The batch was placed under 1 torr vacuum to remove N,N-dimethylformamide dimethyl acetal, which left the crude enamine (22 g, 91.9 mmol) behind. Neat 3-aminopyrazole (17.7 g, 212 mmol) was added to the batch and the mixture was heated at 95° C. for another 19 hours. After cooling, the crude product was diluted with ethyl acetate (10 mL) and adsorbed onto 50 g of silica gel (230-400 mesh), evaporating the solvent in vacuo. This material was loaded onto a column of silica gel (230-400 mesh, 120 g) equilibrated with hexane. Product was isolated by eluting the column with 50% by volume ethyl acetate-hexanes (2 L), collecting a single fraction. Concentration under reduced pressure provided 13 g of product as a mixture of linear and bent isomers. Re-crystallization of this material from boiling ethyl acetate (7 mL) gave the title compound (5.92 g, 25% yield) in 97+% purity.

Preparation 7

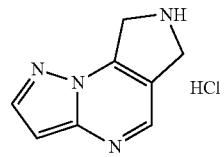

7,8-dihydro-6H-pyrazolo[1,5-a]pyrrolo[3,4-e]pyrimidine hydrochloride salt

A 500 mL single-necked round-bottomed flask was equipped with a magnetic stirrer and stir bar, condenser, heating/cooling bath, nitrogen inlet. The vessel was charged with tert-butyl 6,8-dihydro-7H-pyrazolo[1,5-a]pyrrolo[3,4-e]pyrimidine-7-carboxylate (21.3 g, 81.6 mmol) and MeOH (200 mL). The contents were heated to 65° C. with stirring to give a solution. After cooling the batch to 50° C., aqueous 12 N hydrochloric acid (27.5 mL) was added slowly with care, resulting in an exotherm to 61° C. and gas evolution. After stirring the batch at 60° C. for 1 hour, an aliquot indicated that the reaction was complete. The mixture was chilled in an ice-water bath for 30 minutes, and the precipitated crystalline salt was collected on a filter. The filter cake was rinsed with cold methanol (100 mL) and air dried to provide the title compound (18 g, 112% yield). The title compound free base is prone to oxidize to 7H-pyrazolo[1,5-a]pyrrolo[3,4-e]pyrimidine.

Example 5

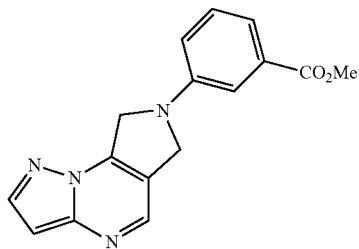

Methyl 3-(6,8-dihydro-7H-pyrazolo[1,5-a]pyrrolo[3,4-e]pyrimidin-7-yl)benzoate

A 250 mL, single-necked, round-bottomed flask was equipped with a magnetic stirrer and stir bar, heating bath, thermocouple, rubber septum and nitrogen line with needle, gas bubbler. The flask was charged with 7,8-dihydro-6H-pyrazolo[1,5-a]pyrrolo[3,4-e]pyrimidine hydrochloride salt (1.7 g, 8.6 mmol), 4,5-bis(diphenylphosphino)-9,9-dimethylxanthene (522 mg, 0.90 mmol), cesium carbonate (5.8 g, 17.8 mmol), methyl 3-bromobenzoate (2.15 g, 10.0 mmol), and a 5:1 mixture by volume of toluene and t-butanol (100 mL). The stirred mixture was degassed by passing nitrogen through it for 5 minutes. Powdered palladium(II) acetate (207 mg, 0.92 mmol) was added rapidly, and the mixture was degassed again for 3 minutes. The stirred batch was heated to 93° C. under nitrogen for 23 hours. The mixture was cooled to 22° C. and filtered through a short pad of silica gel (20 g), rinsing the reactor and the silica gel pad with ethyl acetate (100 mL). The filtrate and rinse were concentrated in vacuo to yield 3.1 g of a solid. This material was swished in a 50% by volume mixture of ethyl acetate and hexanes (40 mL), filtered, and dried under reduced pressure to give the title compound (1.53 g, 61% yield) in 97% purity.

Example 6

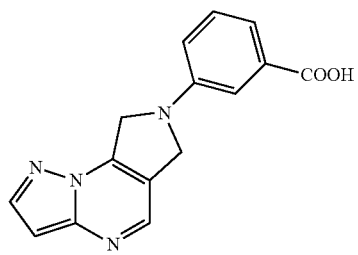

3-(6,8-dihydro-7H-pyrazolo[1,5-a]pyrrolo[3,4-e]pyrimidin-7-yl)benzoic acid

A 1 L, three-necked, round-bottomed flask was equipped with a magnetic stirrer and stir bar, heating bath, condenser, thermocouple and nitrogen inlet. The flask was charged with methyl 3-(6,8-dihydro-7H-pyrazolo[1,5-a]pyrrolo[3,4-e]pyrimidin-7-yl)benzoate (2.5 g, 8.5 mmol), aqueous 3 N sodium hydroxide (13 mL, 39 mmol), tetrahydrofuran (50 mL), and methanol (50 mL). The stirred mixture was heated to 65° C. for 1 hour, at which time analysis by HPLC indicated complete reaction. The batch was cooled to ambient temperature and the pH adjusted to 6.5 with aqueous 3 N hydrochloric acid (22 mL, 66 mmol). After standing for 30 minutes, the batch was filtered through a fritted glass funnel and concentrated under reduced pressure. The resulting solids were slurried with 5:2 by volume methanol-water (35 mL) at ambient temperature for 3 hours. Solids were collected on a fritted glass filter, washed with methanol (5 mL), and dried to constant weight in vacuo to give the title compound as a light beige solid (1.2 g, 54% yield).

Example 7

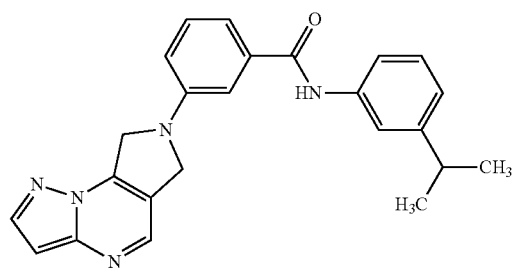 [SMILES: CC(C)c1cccc(NC(=O)c2cccc(N3Cc4cnc5ccnn5c4C3)c2)c1]

3-(6,8-dihydro-7H-pyrazolo[1,5-a]pyrrolo[3,4-e]pyrimidin-7-yl)-N-(3-isopropylphenyl)benzamide To a mixture of 3-(6,8-dihydro-7H-pyrazolo[1,5-a]pyrrolo[3,4-e]pyrimidin-7-yl)benzoic acid (0.40 mmol, 112 mg), N,N-diisopropylethylamine (1.8 mmol, 0.314 mL), and catalytic DMAP in 3.0 mL DMF at rt was added propylphosphonic anhydride solution (50 wt % in EtOAc, 0.52 mmol, 0.309 mL). After 7 min at rt, 3-isopropylaniline (0.60 mmol, 0.085 mL) was added and the reaction stirred at rt for 24 hours. The reaction was quenched with saturated aqueous NaHCO₃ solution, extracted into EtOAc, the EtOAc layer washed with brine, dried with anhydrous Na₂SO₄ and rotary evaporated. The residue was chromatographed eluting with CHCl₃/EtOAc to give the title compound as a light beige solid (30 mg, 19%).

¹H NMR (Acetone-d6) δ: 9.44 (br. s., 1H), 8.67 (s, 1H), 8.23 (d, J=1.8 Hz, 1H), 7.69-7.75 (m, 2H), 7.36-7.46 (m, 3H), 7.27 (t, J=8.1 Hz, 1H), 7.01 (d, J=7.6 Hz, 2H), 6.77 (d, J=1.8 Hz, 1H), 5.12 (t, J=3.1 Hz, 2H), 4.92 (t, J=3.2 Hz, 2H), 2.84-2.99 (m, 1H), 1.26 (d, J=7.0 Hz, 6H).

Example 8

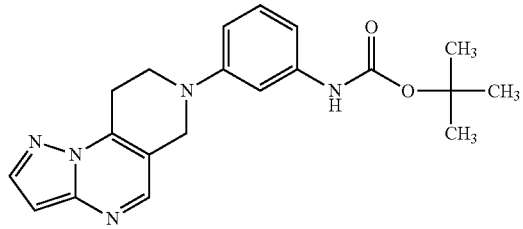 [SMILES: CC(C)(C)OC(=O)Nc1cccc(N2CCc3c(cnc4ccnn34)C2)c1]

tert-Butyl (3-(8,9-dihydropyrazolo[1,5-a]pyrimidin-7(6H)-yl)phenyl)carbamate

A mixture of 6,7,8,9-tetrahydropyrazolo[1,5-a]pyrido[3,4-e]pyrimidine (3.65 g, 20.95 mmol), N-(tert-butoxycarbonyl)-3-bromoanline (8.85 g, 32.52 mmol), SPhos (1.71 g, 4.16 mmol), Pd(OAc)₂ (0.939 g, 4.18 mmol) and Cs₂CO₃ (18.0 g, 55.2 mmol) in toluene (140 mL) stirred at 85° C. for 48 hours. The mixture was cooled to room temperature and filtered over a fritted funnel, washing with EtOAc and acetone. The filter cake was taken up in H₂O and extracted with EtOAc (3×150 mL). The organic extracts were dried (MgSO₄), filtered and concentrated. The initial filtrate was concentrated. The residue was taken up in MeOH and stirred for 2 hours. The solid was filtered off, washed with MeOH and combined with the previous solid to afford the title compound as a light yellow solid (3.4 g, 44.4%).

Example 9

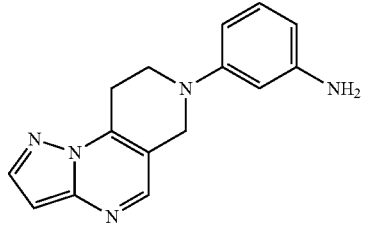

3-(8,9-Dihydropyrazolo[1,5-a]pyrido[3,4-e]pyrimidin-7(6H)-yl)benzenamine

A mixture of tert-Butyl (3-(8,9-dihydropyrazolo[1,5-a]pyrido[3,4-e]pyrimidin-7(6H)-yl)phenyl)carbamate, (3.27 g, 8.94 mmol) and TFA (7.12 mL, 93.6 mmol) in CH₂Cl₂ (116 mL) was stirred at room temperature for 24 hours. The mixture was concentrated, then partitioned between CH₂Cl₂ and 1N NaOH. Extracted with CH₂Cl₂ (3×75 mL). The organic extracts were washed with water, dried (MgSO₄), filtered and concentrated. The residue was taken up in a small amount of MTBE and triturated with hexanes. The resultant solid was filtered off, washed with hexanes and dried under high vacuum to afford the title compound as an orange solid (1.82 g, 77%).

Example 10

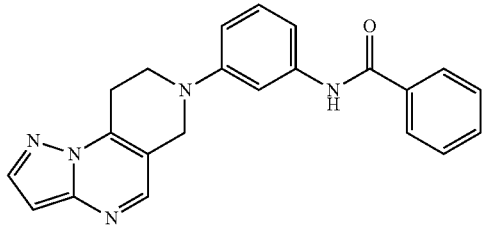 [SMILES: O=C(Nc1cccc(N2CCc3c(cnc4ccnn34)C2)c1)c1ccccc1]

N-[3-(8,9-dihydropyrazolo[1,5-a]pyrido[3,4-e]pyrimidin-7(6H)-yl)phenyl]benzamide To a solution of 3-(8,9-dihydropyrazolo[1,5-a]pyrido[3,4-e]pyrimidin-7(6H)-yl)aniline (0.30 mmol, 79.6 mg) and N,N-diisopropylethylamine (0.60 mmol, 0.105 mL) in 3.0 mL dichloromethane at rt was added benzoyl chloride (0.33 mmol, 0.038 mL). After stirring at rt for 1.5 hours the reaction was quenched with 1.5 mL MeOH, stirred 10 min, and then evaporated. The residue was treated to an EtOAc/saturated aqueous NaHCO$_3$ workup. The resulting oil was chromatographed eluting with EtOAc/CHCl$_3$ and the product triturated with EtOAc to give the title compound as a yellow solid (82 mg, 74%).

$^1$H NMR (DSMO-d6) δ: 10.13 (s, 1H), 8.51 (s, 1H), 8.20 (d, J=1.8 Hz, 1H), 7.95 (d, J=7.3 Hz, 2H), 7.49-7.63 (m, 4H), 7.28-7.33 (m, 1H), 7.19-7.27 (m, 1H), 6.90 (d, J=7.6 Hz, 1H), 6.74 (d, J=1.8 Hz, 1H), 4.49 (s, 2H), 3.77 (t, J=5.7 Hz, 2H), 3.25-3.30 (m, 2H).

Example 11

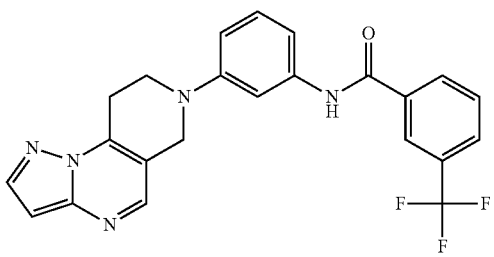

N-[3-(8,9-dihydropyrazolo[1,5-a]pyrido[3,4-e]pyrimidin-7(6H)-yl)phenyl]-3-(trifluoromethyl)benzamide In a manner similar to that described in Example 10, 3-(8,9-dihydropyrazolo[1,5-a]pyrido[3,4-e]pyrimidin-7(6H)-yl)aniline (0.30 mmol, 79.6 mg) and (3-trifluoro methyl) benzoyl chloride (0.315 mmol, 0.047 mL) were reacted to give the title compound as light beige solid (86 mg, 66%).

$^1$H NMR (DSMO-d6) δ: 10.37 (s, 1H), 8.51 (s, 1H), 8.24-8.30 (m, 2H), 8.20 (d, J=2.3 Hz, 1H), 7.97 (d, J=7.6 Hz, 1H), 7.76-7.83 (m, 1H), 7.54-7.57 (m, 1H), 7.22-7.32 (m, 2H), 6.93 (dt, J=7.8, 2.0 Hz, 1H), 6.74 (d, J=2.3 Hz, 1H), 4.50 (s, 2H), 3.78 (t, J=5.7 Hz, 2H), 3.26-3.31 (m, 2H).

Example 12

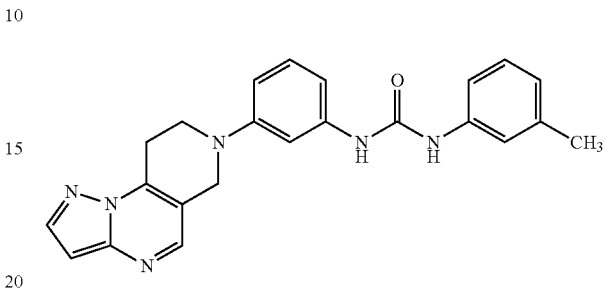

1-[3-(8,9-dihydropyrazolo[1,5-a]pyrido[3,4-e]pyrimidin-7(6H)-yl)phenyl]-3-(3-methylphenyl)urea To a mixture of 3-(8,9-dihydropyrazolo[1,5-a]pyrido[3,4-e]pyrimidin-7(6H)-yl)aniline (0.30 mmol, 79.6 mg) and N,N-diisopropylethylamine (0.60 mmol, 0.105 mL) in 3.5 mL dichloromethane at rt was added meta-tolyl isocyanate (0.45 mmol, 0.057 mL). The reaction was stirred at rt for 1.7 hours, and the resulting precipitate filtered and rinsed with dichloromethane, EtOAc, and 50% EtOAc/hexane to give the title compound as a yellow solid (95 mg, 79%).

$^1$H NMR (DSMO-d6) δ: 8.56 (d, J=1.2 Hz, 2H), 8.51 (s, 1H), 8.19 (d, J=2.3 Hz, 1H), 7.29-7.34 (m, 2H), 7.19-7.24 (m, 1H), 7.15 (td, J=7.9, 2.1 Hz, 2H), 6.84 (dd, J=7.9, 1.2 Hz, 1H), 6.73-6.81 (m, 3H), 4.46 (s, 2H), 3.74 (t, J=5.9 Hz, 2H), 3.27 (t, J=5.6 Hz, 2H), 2.28 (s, 3H).

Preparation 8

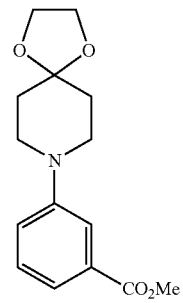

Methyl 2-(1,4-dioxa-8-azaspiro[4.5]decan-8-yl)benzoate

A mixture of 1,4-dioxa-8-azaspiro[4.5]decane (7.0 g, 48.9 mmol), methyl 3-bromobenzoate (12.6 g, 58.6 mmol), BiNAP (3.64 g, 5.84 mmol), Pd(OAc)$_2$ (0.455 g, 2.02 mmol) and Cs$_2$CO$_3$ (45.0 g, 138 mmol) in toluene (210 mL) was stirred at 85° C. for 24 h. The mixture was cooled to room temp and filtered over celite, washing with EtOAc. The filtrate was dried (MgSO$_4$) and concentrated. The residue was purified via column chromatography, eluting with 40% EtOAc/hexanes to afford the title compound as a yellow oil (12.9 g, 95%).

Preparation 9

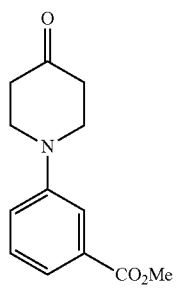

Methyl 3-(4-oxopiperidin-1-yl)benzoate

A mixture of methyl 2-(1,4-dioxa-8-azaspiro[4.5]decan-8-yl)benzoate (2.0 g, 7.21 mmol), pTsOH.H$_2$O (0.137 g, 0.72 mmol), acetone (23.0 mL) and water (40.0 mL) was stirred at 80° C. for 3 days. The mixture was cooled to room temp. and diluted with CH$_2$Cl$_2$. The solution was washed with sat. NaHCO$_3$ and extracted with CH$_2$Cl$_2$ (3×100 mL). The organic extracts were washed with water, dried (MgSO$_4$) and concentrated to afford the title compound (1.57 g, 93%).

Preparation 10

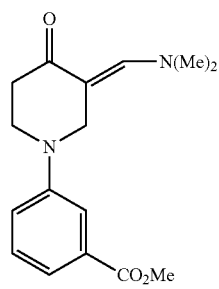

Methyl 3-(3-((dimethylamino)methylene)-4-oxopiperidin-1-yl)benzoate

A mixture of methyl 3-(4-oxopiperidin-1-yl)benzoate (1.0 g, 4.28 mmol), DMF-DMA (1.0 mL, 7.46 mmol) and toluene (8.0 mL) was stirred at 100° C. for 20 h. The mixture was concentrated and dried under high vacuum to afford the title compound (1.23 g, quantitative).

Preparation 11

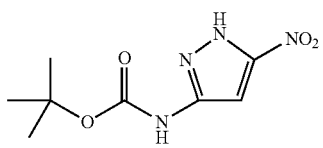

tert-Butyl 5-nitro-1H-pyrazol-3-ylcarbamate

A mixture of 3-nitro-1H-pyrazole-5-carboxylic acid (1.0 g, 6.36 mmol), diphenylphosphorazidate (2.7 mL, 12.5 mmol) and Et$_3$N (1.7 mL, 12.2 mmol) in tBuOH (4.0 mL) was stirred at reflux for 18 hours. The mixture was cooled to room temp and diluted with water. Extracted with EtOAc (4×50 mL). The organic extracts were washed with water, dried (MgSO$_4$) and concentrated. Purified via column chromatography, eluting with 40-50% EtOAc/hexanes to afford the title compound as a light yellow solid (0.452 g).

Preparation 12

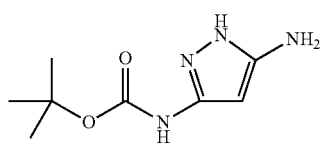

tert-Butyl (5-amino-1H-pyrazol-3-yl)carbamate

To a stirring solution of tert-Butyl 5-nitro-1H-pyrazol-3-ylcarbamate (0.450 g, 1.97 mmol) in EtOAc (16.0 mL) under N$_2$ was added Pd/C (10%, 0.10 g). The mixture was stirred under an atmosphere of H$_2$ at room temp for 18 hours. The mixture was filtered over celite, washing with EtOAc and MeOH. The filtrate was concentrated to an orange oil. Dried under high vacuum to afford the title compound as a brown solid (0.301 g, 77%).

Example 13

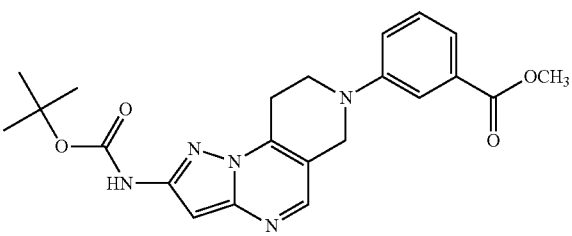

Methyl 3-(2-((tert-butoxycarbonyl)amino)-8,9-dihydropyrazolo[1,5-a]pyrido[3,4-e]pyrimidin-7(6H)-yl)benzoate A mixture of methyl 3-(3-((dimethylamino)methylene)-4-oxopiperidin-1-yl)benzoate (0.145 g, 0.503 mmol) and tert-Butyl (5-amino-1H-pyrazol-3-yl)carbamate (0.150 g, 0.756 mmol) in EtOH (4.0 mL) was stirred at 80° C. for 20 h. The mixture was cooled and concentrated. The residue was washed with MTBE and hexanes. Dried under high vacuum. A mixture of the title compound and methyl 3-(2-((tert-butoxycarbonyl)amino)-5,6-dihydropyrazolo[1,5-a]pyrido[4,3-d]pyrimidin-7(8H)-yl)benzoate was afforded, which was separated by prep HPLC to afford the title compound (0.011 g) and methyl 3-(2-((tert-butoxycarbonyl)amino)-5,6-dihydropyrazolo[1,5-a]pyrido[4,3-d]pyrimidin-7(8H)-yl)benzoate (0.050 g). Prep HPLC Method: Phenomex Luna 100× 21.2 mm, 10 μM, C(18) column; Gradient of 55% H$_2$O and 45% CH$_3$CN; Flow Rate 1 mL/min.; uv @215 nm.

Preparation 13

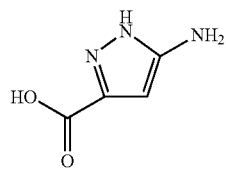

5-Amino-1H-pyrazole-3-carboxylic acid

To a mixture of 3-nitro-1H-pyrazole-5-carboxylic acid (0.50 g, 3.18 mmol) in EtOAc/MeOH (3:1, 10.0 mL) was added a solution of Pearlman's Catalyst (Wet PdOH/C, 20%;

0.050 g) and Degussa Catalyst (Wet PdOH/C, 20%, En101 NE/W; 0.050 g) in EtOAc (2.0 mL). The mixture was stirred under an atmosphere of $H_2$ at room temp. for 20 h. The mixture was purged with $N_2$. A 1N NaOH (3.2 mL) solution was added and the mixture stirred at room temp. for 30 minutes. The mixture was filtered over celite, washing with EtOAc and MeOH. The filtrate was concentrated then acidified to pH=2 with 1N HCl to afford the title compound (0.404 g, quantitative) as a lavender solid. The solid was filtered off, washed with water and dried under high vacuum. No further purification.

Example 14

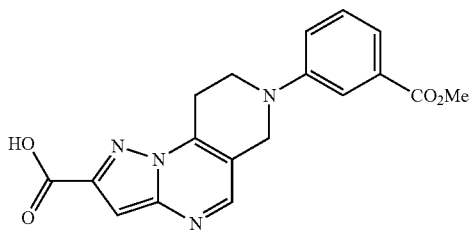

7-(3-Methoxycarbonyl)phenyl)-6,7,8,9-tetrahydropyrazolo[1,5-a]pyrido[3,4-e]pyrimidine-2-carboxylic acid A mixture of methyl 3-(3-(((dimethylamino)methylene)-4-oxopiperidin-1-yl)benzoate (0.606 g, 2.10 mmol) and 5-amino-1H-pyrazole-3-carboxylic acid (0.404 g, 3.18 mmol) in EtOH (8.0 mL) was stirred at 80° C. for 20 h. The mixture was cooled and concentrated. The residue was taken up in $H_2O$ and acidified to pH=2 with 1N HCl. The precipitate was filtered off and washed with water, MTBE and hexanes. Dried under high vacuum to afford the title compound (0.362 g, 49%) as a brown solid.

VEGFR2 and PDGFRβ kinase potencies of select analogs was determined by the following assay:

VEGFR2 Kinase Assay:

Biochemical KDR kinase assays were performed in 96 well microtiter plates that were coated overnight with 75 μg/well of poly-Glu-Tyr (4:1) in 10 mM Phosphate Buffered Saline (PBS), pH 7.4. The coated plates were washed with 2 mls per well PBS+0.05% Tween-20 (PBS-T), blocked by incubation with PBS containing 1% BSA, then washed with 2 mls per well PBS-T prior to starting the reaction. Reactions were carried out in 100 μL reaction volumes containing 2.7 μM ATP in kinase buffer (50 mM Hepes buffer pH 7.4, 20 mM $MgCl_2$, 0.1 mM $MnCl_2$ and 0.2 mM $Na_3VO_4$). Test compounds were reconstituted in 100% DMSO and added to the reaction to give a final DMSO concentration of 5%. Reactions were initiated by the addition 20 ul per well of kinase buffer containing 200-300 ng purified cytoplasmic domain KDR protein (BPS Bioscience, San Diego, Calif.). Following a 15 minute incubation at 30° C., the reactions were washed 2 mls per well PBS-T. 100 μl of a monoclonal anti-phosphotyrosine antibody-peroxidase conjugate diluted 1:10,000 in PBS-T was added to the wells for 30 minutes. Following a 2 mls per well wash with PBS-Tween-20, 100 μl of O-Phenylenediamine Dihydrochloride in phosphate-citrate buffer, containing urea hydrogen peroxide, was added to the wells for 7-10 minutes as a colorimetric substrate for the peroxidase. The reaction was terminated by the addition of 100 μl of 2.5N $H_2SO_4$ to each well and read using a microplate ELISA reader set at 492 nm. $IC_{50}$ values for compound inhibition were calculated directly from graphs of optical density (arbitrary units) versus compound concentration following subtraction of blank values.

VEGFR2 Cellular Assay

Automated FLIPR (Fluorometric Imaging Plate Reader) technology was used to screen for inhibitors of VEGF induced increases in intracellular calcium levels in fluorescent dye loaded endothelial cells. HUVEC (human umbilical vein endothelial cells) (Clonetics) were seeded in 384-well fibronectin coated black-walled plates overnight @ 37° C./5% CO2. Cells were loaded with calcium indicator Fluo-4 for 45 minutes at 37° C. Cells were washed 2 times (Elx405, Biotek Instruments) to remove extracellular dye. For screening, cells were pre-incubated with test agents for 30 minutes, at a single concentration (10 uM) or at concentrations ranging from 0.0001 to 10.0 uM followed by $VEGF_{165}$ stimulation (10 ng/mL). Changes in fluorescence at 516 nm were measured simultaneously in all 384 wells using a cooled CCD camera. Data were generated by determining max-min fluorescence levels for unstimulated, stimulated, and drug treated samples. $IC_{50}$ values for test compounds were calculated from inhibition of VEGF stimulated responses in the absence of inhibitor.

PDGFRβ Kinase Assay

Biochemical PDGFRβ kinase assays were performed in 96 well microtiter plates that were coated overnight with 75 μg of poly-Glu-Tyr (4:1) in 10 mM Phosphate Buffered Saline (PBS), pH 7.4. The coated plates were washed with 2 mls per well PBS+0.05% Tween-20 (PBS-T), blocked by incubation with PBS containing 1% BSA, then washed with 2 mls per well PBS-T prior to starting the reaction. Reactions were carried out in 100 μL reaction volumes containing 36 μM ATP in kinase buffer (50 mM Hepes buffer pH 7.4, 20 mM $MgCl_2$, 0.1 mM $MnCl_2$ and 0.2 mM $Na_3VO_4$). Test compounds were reconstituted in 100% DMSO and added to the reaction to give a final DMSO concentration of 5%. Reactions were initiated by the addition 20 ul per well of kinase buffer containing 200-300 ng purified cytoplasmic domain PDGFR-b protein (Millipore). Following a 60 minute incubation at 30° C., the reactions were washed 2 mls per well PBS-T. 100 μl of a monoclonal anti-phosphotyrosine antibody-peroxidase conjugate diluted 1:10,000 in PBS-T was added to the wells for 30 minutes. Following a 2 mls per well wash with PBS-Tween-20, 100 μl of 0-Phenylenediamine Dihydrochloride in phosphate-citrate buffer, containing urea hydrogen peroxide, was added to the wells for 7-10 minutes as a colorimetric substrate for the peroxidase. The reaction was terminated by the addition of 100 μl of 2.5N $H_2SO_4$ to each well and read using a microplate ELISA reader set at 492 nm. $IC_{50}$ values for compound inhibition were calculated directly from graphs of optical density (arbitrary units) versus compound concentration following subtraction of blank values.

PDGFRβ Cellular Assay

Automated FLIPR (Fluorometric Imaging Plate Reader) technology was used to screen for inhibitors of PDGF-induced increases in intracellular calcium levels in fluorescent dye loaded endothelial cells. NHDF-Ad (Normal Human Dermal Fibroblasts, Adult; Lonza) were seeded in 384-well fibronectin coated black-walled plates overnight @ 37° C./5% CO2. Cells were loaded with calcium indicator Fluo-4 for 45 minutes at 37° C. Cells were washed 2 times (Elx405, Biotek Instruments) to remove extracellular dye. For screening, cells were pre-incubated with test agents for 30 minutes, at a single concentration (10 uM) or at concentrations ranging from 0.0001 to 10.0 uM followed by PDGF-BB stimulation (30 ng/mL). Changes in fluorescence at 516 nm were measured simultaneously in all 384 wells using a cooled CCD camera. Data were generated by determining max-min fluorescence levels for unstimulated, stimulated, and drug treated samples. $IC_{50}$ values for test compounds were calculated from % inhibition of PDGF-BB stimulated responses in the absence of inhibitor.

TABLE 2

In vitro VEGFR2 and PDGFRβ data

| Ex. No. | Structure | VEGFR2 Kinase Assay ($IC_{50}$ nM) | VEGFR2 Cellular Assay ($IC_{50}$ nM) | PDGFR βKinase Assay ($IC_{50}$ nM) | PDGFR βCellular Assay ($IC_{50}$ nM) |
|---|---|---|---|---|---|
| 3 | 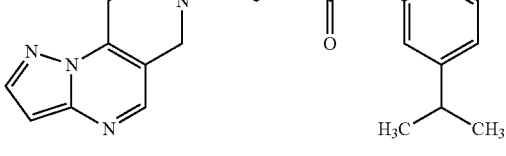 | 8 | 26 | 20 | NA |
| 4 | 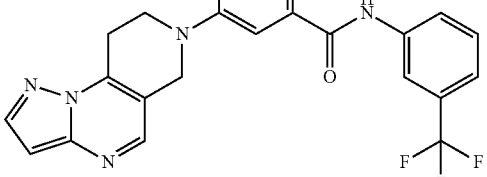 | 6 | 70 | 27 | 192 |
| 7 | 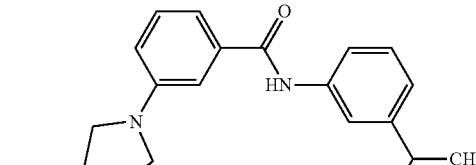 | >10000 | NA | NA | NA |
| 8 | 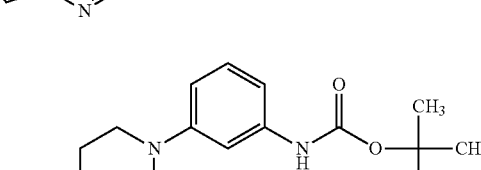 | >10000 | NA | NA | NA |
| 10 | 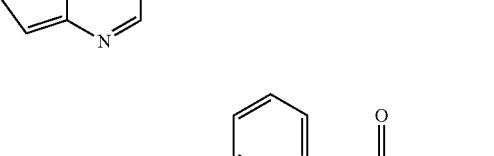 | 101 | NA | 202 | NA |

TABLE 2-continued

In vitro VEGFR2 and PDGFRβ data

| Ex. No. | Structure | VEGFR2 Kinase Assay (IC$_{50}$ nM) | VEGFR2 Cellular Assay (IC$_{50}$ nM) | PDGFR βKinase Assay (IC$_{50}$ nM) | PDGFR βCellular Assay (IC$_{50}$ nM) |
|---|---|---|---|---|---|
| 11 | 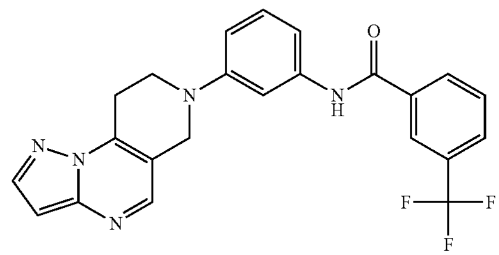 [SMILES: O=C(Nc1cccc(N2CCc3c(cnc4ccnn34)C2)c1)c1cccc(C(F)(F)F)c1] | 6 | NA | 21 | NA |
| 12 | 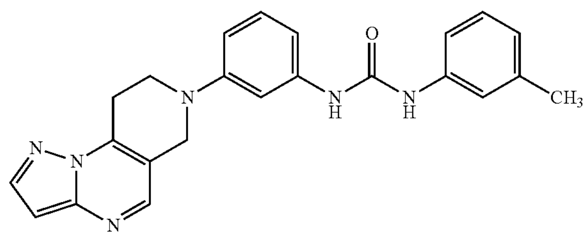 [SMILES: Cc1cccc(NC(=O)Nc2cccc(N3CCc4c(cnc5ccnn45)C3)c2)c1] | 27 | NA | 32 | NA |

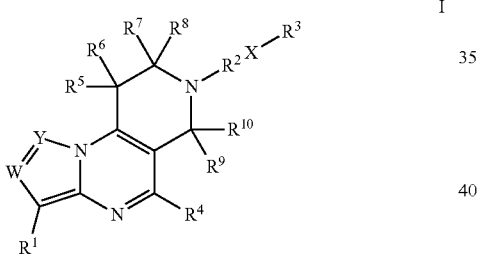

We claim:

1. A compound represented by Formula I, its enantiomers, diastereoisomers, tautomers, or a pharmaceutically acceptable salt thereof:

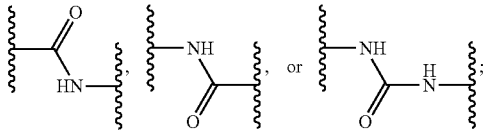

I wherein:
 $R^1$ is H;
 $R^2$ is substituted or unsubstituted heterocycle or is substituted or unsubstituted aryl;
 $R^3$ is substituted or unsubstituted heterocycle or is substituted or unsubstituted aryl;
 $R^4$ is H;
 $R^5$ is H or substituted or unsubstituted $C_{1-8}$ alkyl;
 $R^6$ is H or substituted or unsubstituted $C_{1-8}$ alkyl;
 $R^7$ is H or substituted or unsubstituted $C_{1-8}$ alkyl;
 $R^8$ is H or substituted or unsubstituted $C_{1-8}$ alkyl;
 $R^9$ is H or substituted or unsubstituted $C_{1-8}$ alkyl;
 $R^{10}$ is H or substituted or unsubstituted $C_{1-8}$ alkyl;
 X is Y is N;
W is $CR^{12}$;
$R^{12}$ is hydrogen or $C(O)OR^{17}$.

2. A compound according to claim 1, wherein:
X is

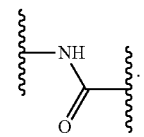 [SMILES: *NC(*)=O]

3. A compound according to claim 1, wherein:
X is

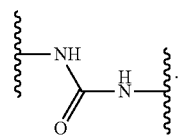

4. A compound according to claim 1, wherein:
X is

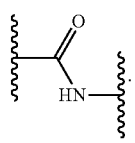

5. A compound according to claim 1, wherein:
 $R^1$ is H;
 $R^2$ is substituted or unsubstituted heterocycle or substituted or unsubstituted aryl;

R³ is substituted or unsubstituted heterocycle or substituted or unsubstituted aryl;
R⁴ is H;
R⁵ is H;
R⁶ is H;
R⁷ is H;
R⁸ is H;
R⁹ is H;
R¹⁰ is H;
X is

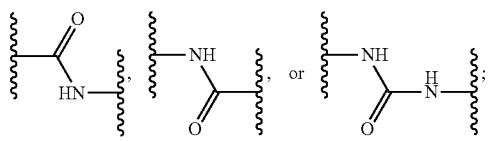

Y is N;
W is CR¹²;
R¹² is hydrogen or C(O)OR¹⁷.

6. A compound according to claim 1, wherein:
R¹ is H;
R² is substituted or unsubstituted aryl;
R³ is substituted or unsubstituted aryl;
R⁴ is H;
R⁵ is H;
R⁶ is H;
R⁷ is H;
R⁸ is H;
R⁹ is H;
R¹⁰ is H;
X is

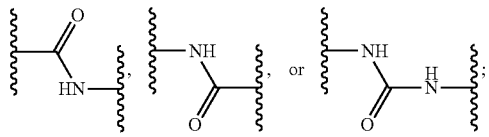

Y is N;
W is CR¹²;
R¹² is hydrogen or C(O)OR¹⁷; and
R¹⁷ is H or substituted or unsubstituted C$_{1-8}$ alkyl.

7. A pharmaceutical composition comprising as active ingredient a therapeutically effective amount of a compound according to claim 1 and a pharmaceutically acceptable adjuvant, diluent or carrier.

8. A compound, the compound being methyl 3-(8,9-dihydropyrazolo[1,5-a]pyrido[3,4-e]pyrimidin-7(6H)-yl)benzoate, or a pharmaceutically acceptable salt thereof.

9. A compound, the compound being 3-(8,9-dihydropyrazolo[1,5-a]pyrido[3,4-e]pyrimidin-7(6H)-yl)benzoic acid, or a pharmaceutically acceptable salt thereof.

10. A compound according to claim 1, wherein the compound is 3-(8,9-dihydropyrazolo[1,5-a]pyrido[3,4-e]pyrimidin-7(6H)-yl)-N-(3-isopropylphenyl)benzamide, or a pharmaceutically acceptable salt thereof.

11. A compound according to claim 1, wherein the compound is 3-(8,9-dihydropyrazolo[1,5-a]pyrido[3,4-e]pyrimidin-7(6H)-yl)-N-[3-(trifluoromethyl)phenyl]benzamide, or a pharmaceutically acceptable salt thereof.

12. A compound, wherein the compound is methyl 3-(6,8-dihydro-7H-pyrazolo[1,5-a]pyrrolo[3,4-e]pyrimidin-7-yl)benzoate, or a pharmaceutically acceptable salt thereof.

13. A compound, wherein the compound is 3-(6,8-dihydro-7H-pyrazolo[1,5-a]pyrrolo[3,4-e]pyrimidin-7-yl)benzoic acid, or a pharmaceutically acceptable salt thereof.

14. A compound, wherein the compound is 3-(6,8-dihydro-7H-pyrazolo[1,5-a]pyrrolo[3,4-e]pyrimidin-7-yl)-N-(3-isopropylphenyl)benzamide.

15. A compound, wherein the compound is tert-butyl (3-(8,9-dihydropyrazolo[1,5-a]pyrido[3,4-e]pyrimidin-7(6H)-yl)phenyl)carbamate, or a pharmaceutically acceptable salt thereof.

16. A compound, wherein the compound is 3-(8,9-dihydropyrazolo[1,5-a]pyrido[3,4-e]pyrimidin-7(6H)-yl)benzenamine, or a pharmaceutically acceptable salt thereof.

17. A compound according to claim 1, wherein the compound is N-[3-(8,9-dihydropyrazolo[1,5-a]pyrido[3,4-e]pyrimidin-7(6H)-yl)phenyl]benzamide, or a pharmaceutically acceptable salt thereof.

18. A compound according to claim 1, wherein the compound is N-[3-(8,9-dihydropyrazolo[1,5-a]pyrido[3,4-e]pyrimidin-7(6H)-yl)phenyl]-3-(trifluoromethyl)benzamide, or a pharmaceutically acceptable salt thereof.

19. A compound according to claim 1, wherein the compound is 1-[3-(8,9-dihydropyrazolo[1,5-a]pyrido[3,4-e]pyrimidin-7(6H)-yl)phenyl]-3-(3-methylphenyl)urea, or a pharmaceutically acceptable salt thereof.

20. A compound, wherein the compound is Methyl 3-(2-((tert-butoxycarbonyl)amino)-8,9-dihydropyrazolo[1,5-a]pyrido[3,4-e]pyrimidin-7(6H)-yl)benzoate, or a pharmaceutically acceptable salt thereof.

21. A compound, wherein the compound is 7-(3-Methoxycarbonyl)phenyl)-6,7,8,9-tetrahydropyrazolo[1,5-a]pyrido[3,4-e]pyrimidine-2-carboxylic acid, or a pharmaceutically acceptable salt thereof.

* * * * *